United States Patent
O'Neill

(10) Patent No.: US 11,039,752 B2
(45) Date of Patent: Jun. 22, 2021

(54) NON-INVASIVE SENSOR APPARATUS AND METHOD FOR ASSESSING CARDIAC PERFORMANCE

(71) Applicant: Accumed Systems Inc., Ann Arbor, MI (US)

(72) Inventor: William W. O'Neill, Ann Arbor, MI (US)

(73) Assignee: Accu-Therm Systems, Inc., Ann Arbor, MI (US)

( * ) Notice: Subject to any disclaimer, the term of this patent is extended or adjusted under 35 U.S.C. 154(b) by 912 days.

(21) Appl. No.: 14/029,755

(22) Filed: Sep. 17, 2013

(65) Prior Publication Data

US 2014/0081089 A1 Mar. 20, 2014

Related U.S. Application Data

(60) Provisional application No. 61/701,868, filed on Sep. 17, 2012.

(51) Int. Cl.
| | |
|---|---|
| *A61B 5/0205* | (2006.01) |
| *A61B 5/01* | (2006.01) |
| *A61B 5/00* | (2006.01) |
| *A61B 5/145* | (2006.01) |
| *A61B 5/053* | (2021.01) |
| *A61B 5/1455* | (2006.01) |
| *A61B 5/026* | (2006.01) |

(52) U.S. Cl.
CPC ............ *A61B 5/02055* (2013.01); *A61B 5/01* (2013.01); *A61B 5/015* (2013.01); *A61B 5/0205* (2013.01); *A61B 5/026* (2013.01); *A61B 5/053* (2013.01); *A61B 5/14539* (2013.01); *A61B 5/14542* (2013.01); *A61B 5/14551* (2013.01); *A61B 5/6828* (2013.01); *A61B 5/6833* (2013.01); *A61B 5/6898* (2013.01); *A61B 5/72* (2013.01); *A61B 5/742* (2013.01); *A61B 5/7475* (2013.01); *A61B 5/6831* (2013.01)

(58) Field of Classification Search
CPC ......... A61B 5/00; A61B 5/0408; A61B 5/416; A61B 5/04087; G06F 19/3418
USPC .................. 600/301, 388, 391, 483, 300
See application file for complete search history.

(56) References Cited

U.S. PATENT DOCUMENTS

| | | | | |
|---|---|---|---|---|
| 2003/0092975 | A1* | 5/2003 | Casscells, III | A61B 5/01 600/300 |
| 2010/0298718 | A1* | 11/2010 | Gilham | H04W 16/10 600/484 |
| 2011/0077497 | A1* | 3/2011 | Oster | A61B 5/0002 600/372 |
| 2011/0213559 | A1* | 9/2011 | Pollack | A61B 5/7221 702/19 |
| 2012/0095304 | A1* | 4/2012 | Biondi | A61B 5/7282 600/301 |
| 2012/0136231 | A1* | 5/2012 | Markel | A41D 19/0027 600/388 |

* cited by examiner

*Primary Examiner* — William J Levicky
*Assistant Examiner* — Alexander M Eisenberg
(74) *Attorney, Agent, or Firm* — Carlson, Gaskey & Olds, P.C.

(57) ABSTRACT

Non-invasive sensor apparatus and method for assessing cardiac performance. A wide variety of different sensor components can capture sensor readings relating to patient attributes. Those sensor readings can then be compared by a processor component to derive a cardiac performance indicator relating to the patient.

15 Claims, 12 Drawing Sheets

NON-INVASIVE SENSOR APPARATUS AND METHOD FOR ASSESSING CARDIAC PERFORMANCE

RELATED APPLICATIONS

This utility patent application claims priority to the provisional patent application titled "SENSOR APPARATUS AND METHOD" (Ser. No. 61/701,868) filed on Sep. 17, 2012, the contents of which are hereby incorporated by reference in its entirety.

BACKGROUND OF THE INVENTION

The invention is a non-invasive sensor apparatus and method for assessing cardiac performance (collectively the "apparatus").

I. Importance of Cardiac Performance

The circulation of blood is essential for a healthy body. Blood provides organs and individual cells with the nutrients necessary to sustain life. Blood also removes cellular metabolic waste products from the body. At the center of the cardiovascular system is the heart, an organ responsible for pushing blood throughout the body. The heart functions as a pump at the center of a complex network of arteries and veins that make up the cardiovascular system. The cardiovascular system is thus responsible for the delivery of nutrients and the removal of certain wastes throughout the body. The performance of the cardiovascular system can be evaluated in terms of cardiac output.

Unfortunately, age, disease, trauma, and/or other ailments can hinder the distribution of blood throughout the body. Cardiovascular diseases are a serious health problem in the United States and elsewhere.

II. Cardiovascular Diseases Cause Death

According to the World Health Organization ("WHO"), cardiovascular diseases are the number one cause of death in world. An estimated 17.3 million people died of cardiovascular diseases in 2008, a number that represents 30% of all deaths occurring in that year. According to WHO estimates, the number of deaths caused by cardiovascular diseases will reach 23.4 million by 2030.

The Centers for Disease Control and Prevention ("CDC") report that "[c]ardiovascular disease is the leading killer in every racial and ethnic group in America." Many health problems in the United States are either rooted in or manifested as cardiovascular disease. The most common type of heart disease in the United States is coronary artery disease ("CAD"). CAD occurs when plaque builds up in the arteries that supply blood to the heart. This can cause the arteries to narrow over time in a process called atherosclerosis. Plaque buildup can also cause chest pain or discomfort resulting from the inadequate supply of blood to the heart muscle, a condition known as angina. Over time CAD can lead to an irregular heartbeat, a condition known as arrhythmia, and even heart failure.

III. Inadequacy of Non-Invasive Techniques

The life of every human being depends on the continuous presence of sufficient cardiac performance. Unfortunately, prior art tests of cardiac performance such as the insertion of a Swan-Ganz thermal dilution catheter into the pulmonary artery, and other similar tests are invasive, time consuming, and expensive. As a result, many patients with ultimately serious conditions go untested until after the underlying problems become severe.

The diagnosis and treatment of patients would benefit from a non-invasive technique for assessing cardiac performance.

SUMMARY OF THE INVENTION

The invention is a non-invasive sensor apparatus and method for assessing cardiac performance (collectively the "apparatus").

The apparatus can utilize non-invasive sensor readings captured from the skin of the patient to generate an indicator of the patient's cardiac performance. Different embodiments of the apparatus can involve a different number of sensors, different sensor types, different sensor configurations, and different display and processor capabilities.

A wide range of different types of sensor readings can be utilized, including but not limited to temperature, pH, electrical connectivity, and oxygen saturation.

Different embodiments of the apparatus can integrate and communicate with external devices to different degrees, with some embodiments of the apparatus being intended to operate as stand lone devices and other embodiments intended to communicate with a potential range of general purpose and/or process specific devices.

The apparatus can be utilized on a wide variety of different parts of the body of the patient, although it may be particularly desirable to capture sensor readings on the arms or legs because of the ability to compare and contrast sensor readings taken at the core of the body with sensor readings taken at the extremities of an appendage.

A wide variety of different cardiac performance heuristics can be used to calculate a wide variety of different cardiac performance indicators. For example, an arterial perfusion heuristic could be used to generate an arterial perfusion indicator.

In many embodiments of the apparatus, a gradient of sensor readings with respect to sensor location on the body will be the primary input for deriving the cardiac performance indicator. In alternative embodiments, additional factors such as sensor readings over time, other patient data accessible on medical records, ambient temperature and other sensor readings at the location of the sensors, and/or operating parameters inputted on behalf of the provider can impact the way that a cardiac performance heuristic will generate a cardiac performance indicator.

BRIEF DESCRIPTION OF THE DRAWINGS

Many features and inventive aspects of the apparatus are illustrated in the following drawings.

DETAILED DESCRIPTION

The invention is a non-invasive sensor apparatus and method for assessing cardiac performance (collectively the "apparatus").

I. Overview

Figure 1A:
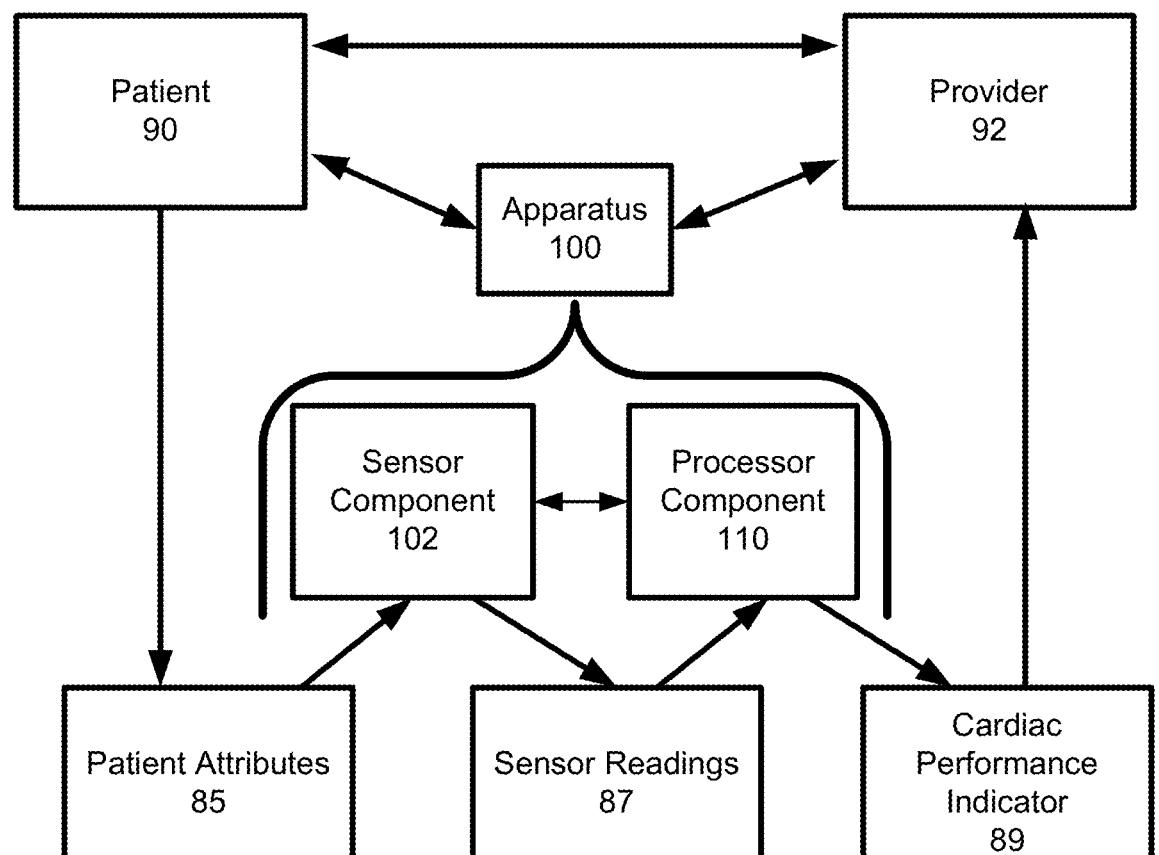
FIG. 1a is a block diagram illustrating an example of interaction between a patient and healthcare provider using the apparatus, and some of the different components and data elements that can be incorporated into the apparatus.

FIG. 1a is a block diagram illustrating an example of interaction between a patient 90 and healthcare provider 92 using the apparatus 100, and some of the different components and data elements that can be incorporated into the apparatus 100.

Patients 90 possess patient attributes 85 which can be detected by a sensor component 102 in the form of a sensor reading 87. A processor component 110 can derive a cardiac performance indicator 89 by analyzing the sensor readings 87 captured by the sensor component 102.

The human body is a collection of organ systems working together to perform the tasks and meet the needs of the body. Blood provides oxygen, nutrients, and enzymes to the body. It also carries away cellular metabolic waste products. Blood flow is managed by the vascular system, a network of arteries and veins through which the heart pumps blood.

Sufficient cardiac output is necessary to sustain life. The impact of insufficient cardiac output can manifest itself in a variety of ways, particularly in the extremities of the body such as legs and arms of a human being. These manifestations, if promptly detected, can serve as a valuable advance warning to providers 92 and patients 90 alike. The early symptoms of insufficient cardiac output can serve as a valuable opportunity that can be exploited for the betterment of patients 90. The symptoms of insufficient cardiac output can be detected in a non-invasive manner when the patient 90 is not suffering from severely insufficient cardiac output, and such early detection can maximize the possibility that steps can be taken to avoid more advanced implications.

The apparatus 100 can utilize sensor readings 87 to non-invasively derive important cardiac performance indicators 89 where prior art techniques would require far more invasive, time consuming, expensive, and inconvenient detection techniques.

A. The Apparatus is a Way for Providers to Interact with Patients

As illustrated in FIG. 1a, the apparatus 100 is a means by which providers 92 interact with their patients 90. The functionality of the apparatus 100 is intended to be part of the delivery system of healthcare to a patient 90 by one or more providers 92.

1. Patients

A patient 90 is typically a human being, although the apparatus 100 (or alternative variations thereof) can also be used in the treatment of potentially any organism, particularly other mammals.

In the context of human beings, patients 90 can vary widely in terms of age, size, gender, weight, medical status, and other attributes.

2. Providers

A provider 92 is typically a healthcare professional such as a physician. In many contexts, the provider could also be a physician's assistant, nurse, technician, paramedic, home health care provider, family or friend that provides care, or other person who assists the physician. In some contexts, patients 90 may act as their own health care providers 92.

The range of potential providers 92 who may find the apparatus 100 desirable is commensurate with the broad range of contexts that the apparatus 100 can be used. For example, in the context of treating animals, the provider 92 could be a veterinarian or veterinarian's assistant. In the context of human patients 90, the apparatus 100 can be used in the context of a variety of different treatment protocols and a variety of different medical conditions.

B. The Apparatus is Comprised of Component Parts

As illustrated in FIG. 1a, the apparatus 100 is comprised of a sensor component 102 for the capturing of sensor readings 87 and a processor component that analyzes those sensor readings 87 to derive a cardiac performance indicator 89.

1. Sensor Component

A sensor component 102 is a means by which information in the form of sensor readings 87 is provided to a processor component 89 for analysis leading to the deriving of a cardiac performance indicator 89 by the apparatus. Different embodiments of the apparatus 100 can involve different numbers of sensor components 102 placed at a different number of locations on a patient 90. By comparing/contrasting sensor readings 87 from different locations of the patient 90, inadequate cardiac output can be detected by the apparatus 100.

Figure 3A:
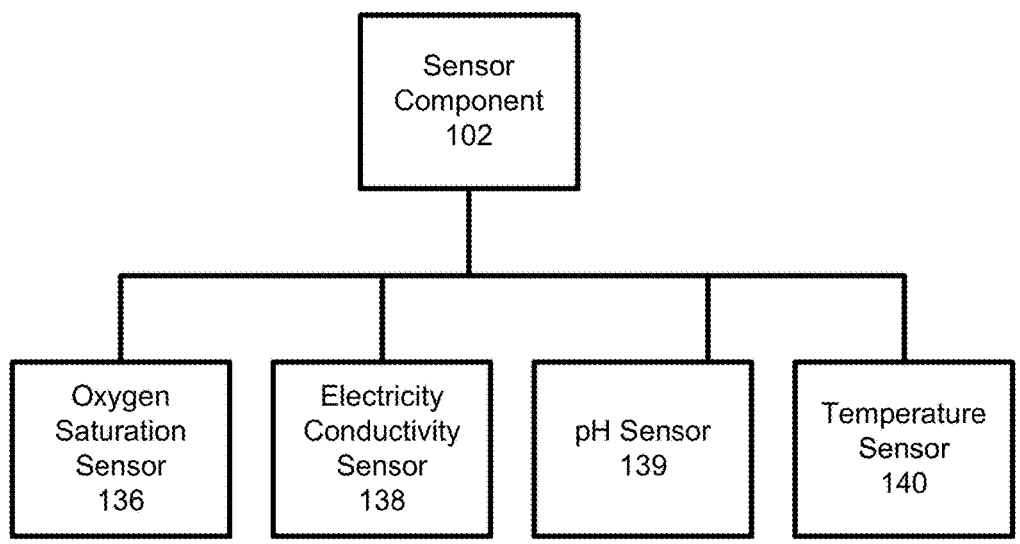
FIG. 3a is a hierarchy diagram illustrating an example of different categories of sensor components that can be included in different embodiments of the apparatus.

Different embodiments of the apparatus 100 can also involve different types of sensor components 102 that measure different types of patient attributes 85. As illustrated in FIG. 3a, the sensor components 102 used by the apparatus 100 can include temperature sensors 140 that detect cardiac output issues through differences in skin temperature, pH sensors 139 that detect cardiac output issues through differences in acidity levels, electricity conductivity sensors 138 that detect cardiac output issues through differences in electrical conductivity, oxygen saturation sensors 136 which detect cardiac output issues through differences in oxygen saturation, as well as other types of sensors.

2. Processor Component

Returning to FIG. 1a, a processor component 110 is the mechanism by which the sensor readings 87 of the sensor components 102 are utilized to derive cardiac performance indicators 89. In some embodiments, the processor component 110 may simply be means to organize the data of the sensor readings 87 into a meaningful display. In other embodiments, more advanced processing can be performed.

Computing power can be used to transform the apparatus 100 from a mere reporting device to a device that can be configured to address certain conditions and operating parameters. In some embodiments of the apparatus 100, the processor component 110 has the capacity to function as a general purpose computer, i.e. possesses the ability to run software, install updates, and store data.

C. Apparatus as a Processor of Data

The purpose of the apparatus 100 is to assess the cardiac performance status of the patient 90 that can be detected through non-invasive sensor readings 87 captured from the skin of the patient 90. Sensor readings 87 can relate to a wide variety of different patient attributes 85 that can be relevant in assessing the cardiac performance of the patient 90, i.e. deriving cardiac performance indicators 89 pertaining to the patient 90.

1. Patient Attributes

A patient attribute 85 is potentially any attribute relating to the patient 90 that can be relevant to assessing the cardiac performance of the patient 90. Some patient attributes 85 can be captured in the form of sensor readings 87, such as temperature measurements, pH levels, electricity conductivity metrics, oxygen saturation levels, and other detectible phenomenon. Other types of patient attributes 85 such as medical history, age, etc. may not be detectible by a sensor component 102 but may still be able to be integrated into the processing of the apparatus 100 through a variety of information technology mechanisms.

2. Sensor Readings

A sensor reading 87 is the output of a sensor component 102 that relates to one or more patient attributes 85. Sensor readings 87 are the primary means by which the processor component 110 is provided with sufficient information to generate cardiac performance indicators 89.

3. Cardiac Performance Indicators

A cardiac performance indicator 89 is the output of the apparatus 100. A cardiac performance indicator 89 is an indication of cardiac performance (i.e. health) of the patient 90. Such indicators 89 can vary from the mere display of data in a usable form (see FIGS. 1f and 1g) to complex outputs involving a potentially wide variety of different inputs beyond sensor readings 87 (see FIG. 1e). As illustrated in FIG. 1e, there are different types of cardiac performance indicators 89 including but not limited to arterial perfusion indicators 91, systematic vascular resistance values 93, and cardiac output estimate 95. Some embodiments of the apparatus 100 can provide users with multiple types of cardiac performance indicators 89, as well as the ability to selectively influence how such indicators 89 are derived and displayed.

D. Process for Using the Apparatus

Figure 1B:
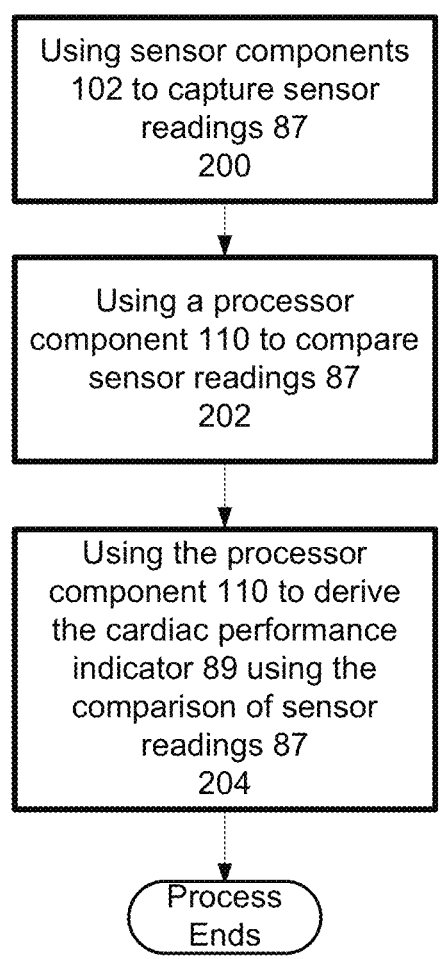
FIG. 1b is a flow chart diagram illustrating an example of the apparatus being used to derive a cardiac performance indicator from sensor readings captured by sensor components.

FIG. 1b is a flow chart diagram illustrating an example of the apparatus 100 being used by a provider 92 or other user to create a cardiac performance indicator 89.

At 200, sensor components 102 are used to capture sensor readings 87 from the patient 90.

At 202, a processor component 110 is used to compare the sensor readings 87 captured at 200 above. In some embodiments of the process, current sensor readings 87 may also be compared with prior sensor readings 87, sensor readings 87 captured from other locations on the patient 90, and other sources of information (see FIG. 1e).

Returning to FIG. 1b, at 204, the processor component 110 is then used to derive the cardiac performance indicator 89 on the basis of the sensor readings 87 and potentially other inputs to the processor component 110.

E. Locations on the Body

Virtually any location on the body of the patient 90 can be used to position a sensor component 102 for the purposes of capturing sensor readings 87. A human being is a collection of organ systems working together to perform the tasks and meet the needs of the body. Blood flows throughout the body, and thus the implications of insufficient cardiac performance are potentially detectible in a wide variety of different locations in a wide variety of different ways. However, for the purposes of evaluating cardiac performance problems through non-invasive sensor readings 87, some locations on the body are better suited than others to assist providers 92 in identifying problems as soon as possible.

Figure 1C:
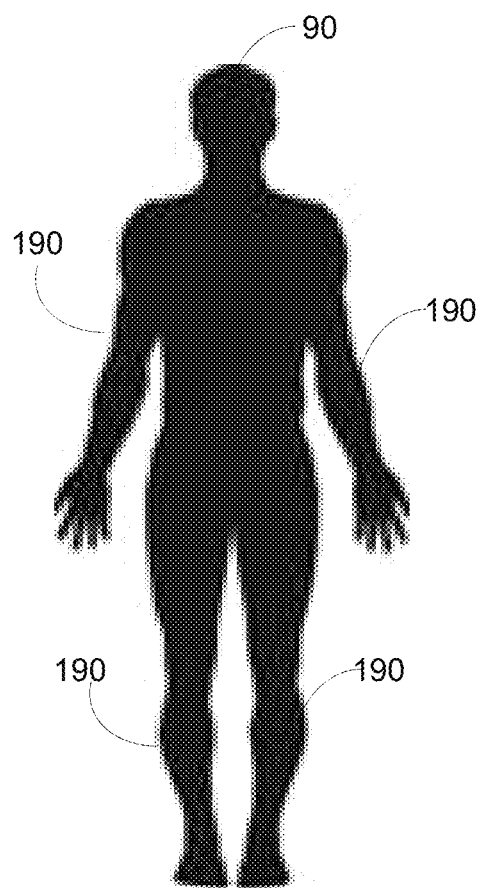
FIG. 1c is a diagram illustrating an example of a human being with four appendages as a patient.

FIG. 1c is a diagram illustrating a human being as the patient 90. Like most human beings, the illustration discloses four large appendages 190 or limbs in the form of two legs and two arms. In many embodiments of the apparatus 100, locations on an appendage 190 such as an arm or leg will be the desirable location for the apparatus 100 to be used because such locations will highlight or even amplify the impact of relatively small differences in cardiac performance.

Figure 1D:
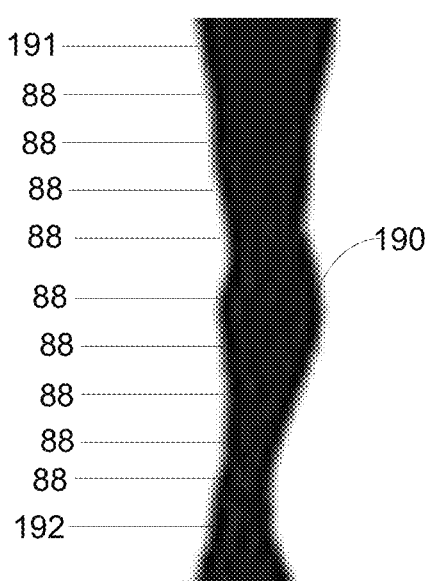
FIG. 1d is a diagram illustrating a close-up view of an appendage displayed in FIG. 1c.
Figure 1E:
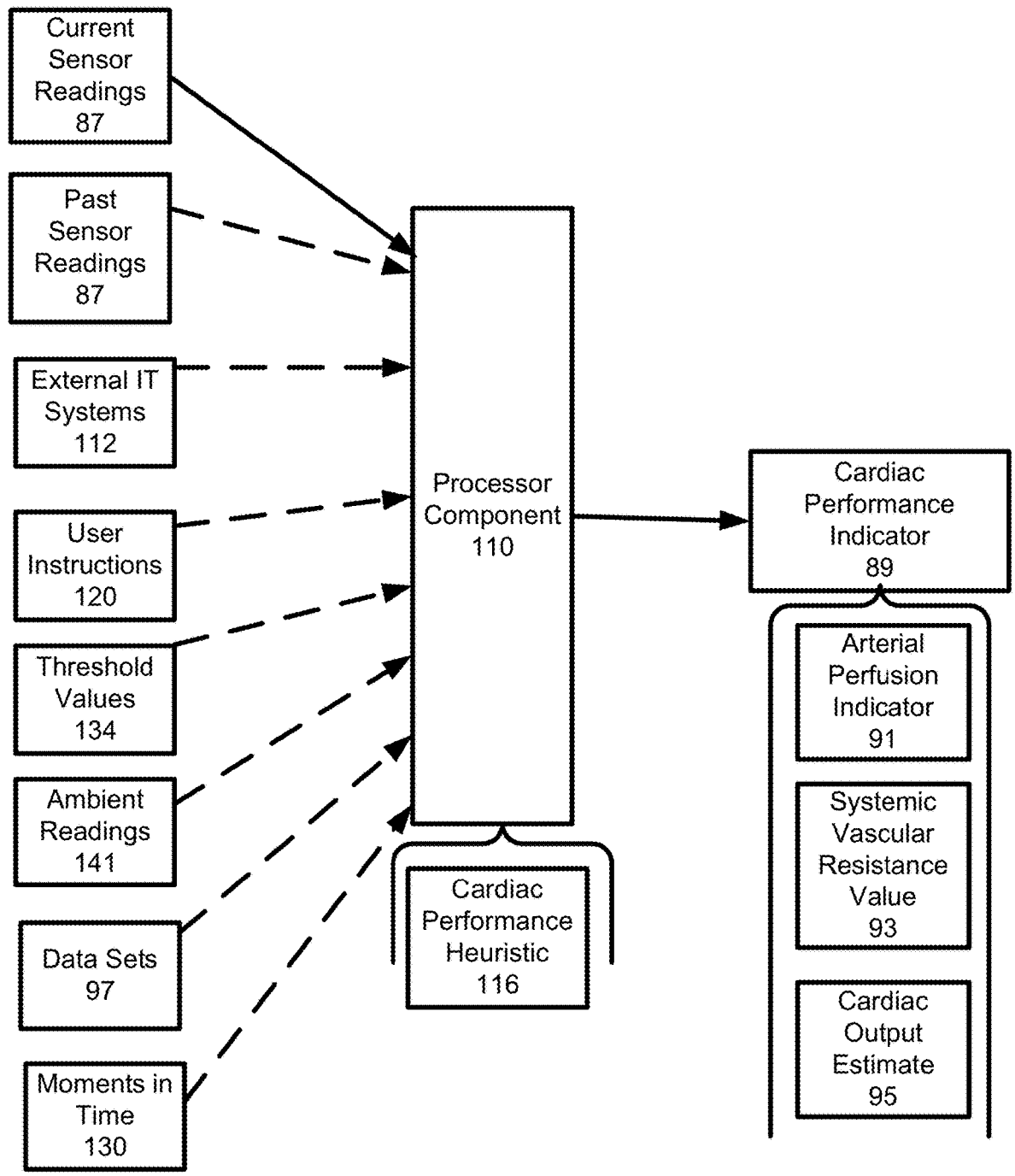
FIG. 1e is an input-output diagram illustrating an example of the different inputs that can impact the cardiac performance indicator generated by the apparatus.

FIG. 1d is a close-up view of one of the legs illustrated in FIG. 1c. As illustrated in the figure, numerous potential locations 88 on the patient 90 exist for the positioning of sensor components. As illustrated in FIG. 1d, many potential locations 88 for sensor components 102 can exist between a core location 191 of the appendage 190 (i.e. a location close to the torso) and an extremity location 192 on the other end of the appendage 190.

In many embodiments of the apparatus 100, positioning sensors components 102 from a core location 191 to an extremity location 192 will provide the best opportunity for early non-invasive detection of cardiac performance problems.

E. Input Factors that can Influence the Resulting Output

FIG. 1e is an input-output diagram illustrating an example of the different inputs that can impact the cardiac performance indicator 89 generated by the apparatus 100. As illustrated in FIG. 1e, there are a wide variety of inputs that can influence the output of the apparatus 100. Similarly, there is a also a wide variety of different cardiac performance indicators 89 that can be generated as outputs by the apparatus.

The processor component 110 of the apparatus 100 can use one or more different cardiac performance heuristics 116 to generate cardiac performance indicators 89 (i.e. outputs) from the sensor readings 87 and other form of inputs indicated in the figure.

1. Inputs

The different types of inputs that can impact the deriving of the cardiac performance indicator 89 include but are not limited to: (a) current sensor readings 87 from the current locations 88 of the sensor components 102 for the apparatus 100; (b) past sensor readings 87; (c) external IT systems 112 with access to data relating to the patient 90; (d) user instructions 120 made available to the apparatus 100 by a provider 92 or in some instances even a patient 90; (e) threshold values 134 that may or may not be individually tailored to the patient 90; (f) ambient readings 141 of the sensor components 102 in an effort to avoid false positive and false negative results; and (g) data sets 97 that potentially include data from multiple apparatuses 100 taken from multiple locations 88 over multiple moments in time 130.

2. Outputs

The outputs of the apparatus 100 can vary widely from embodiment to embodiment both in terms of substantive processing as well as with respect to presentation.

a. Substantive Variations

As illustrated in FIG. 1e, the different embodiments of cardiac performance indicators 89 can include arterial perfusion indicators 91, systemic vascular resistance values 93, cardiac output estimates 95, and other metrics which are discussed in greater detail below.

b. Presentation Variations

Figure 1F:
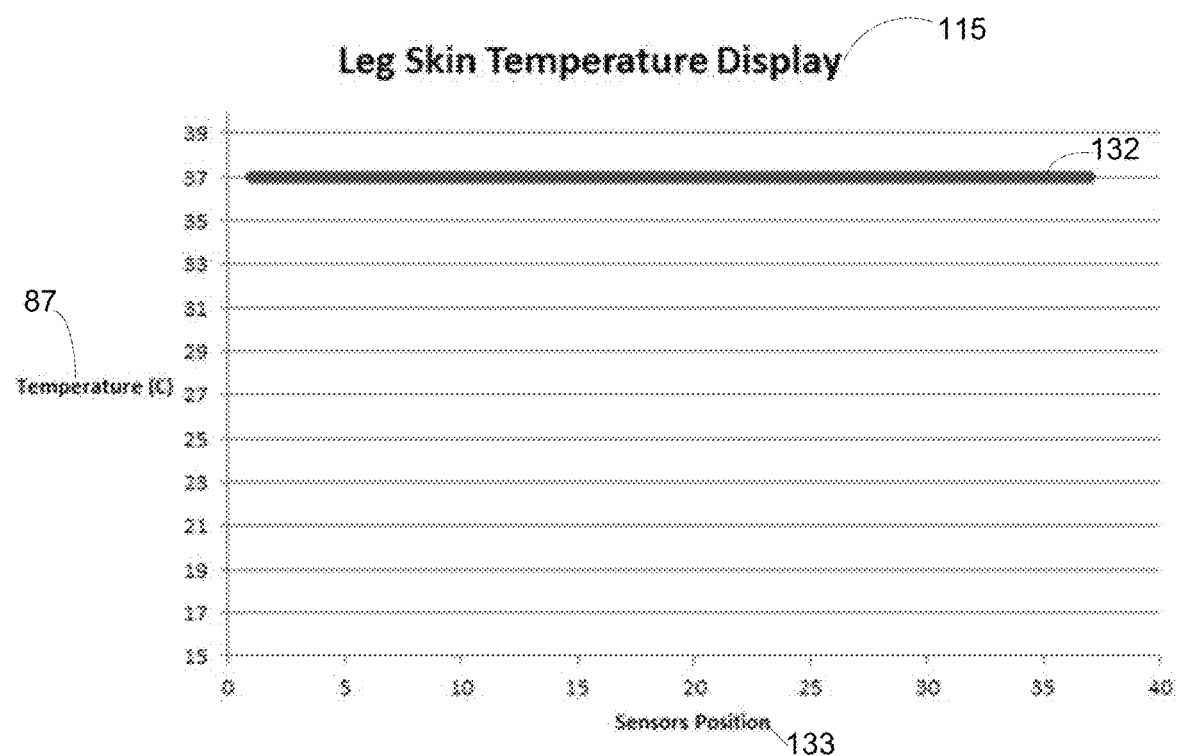
FIG. 1f is an example of a display format for a gradient in which the cardiac performance indicator indicates healthy cardiac performance.
Figure 1G:
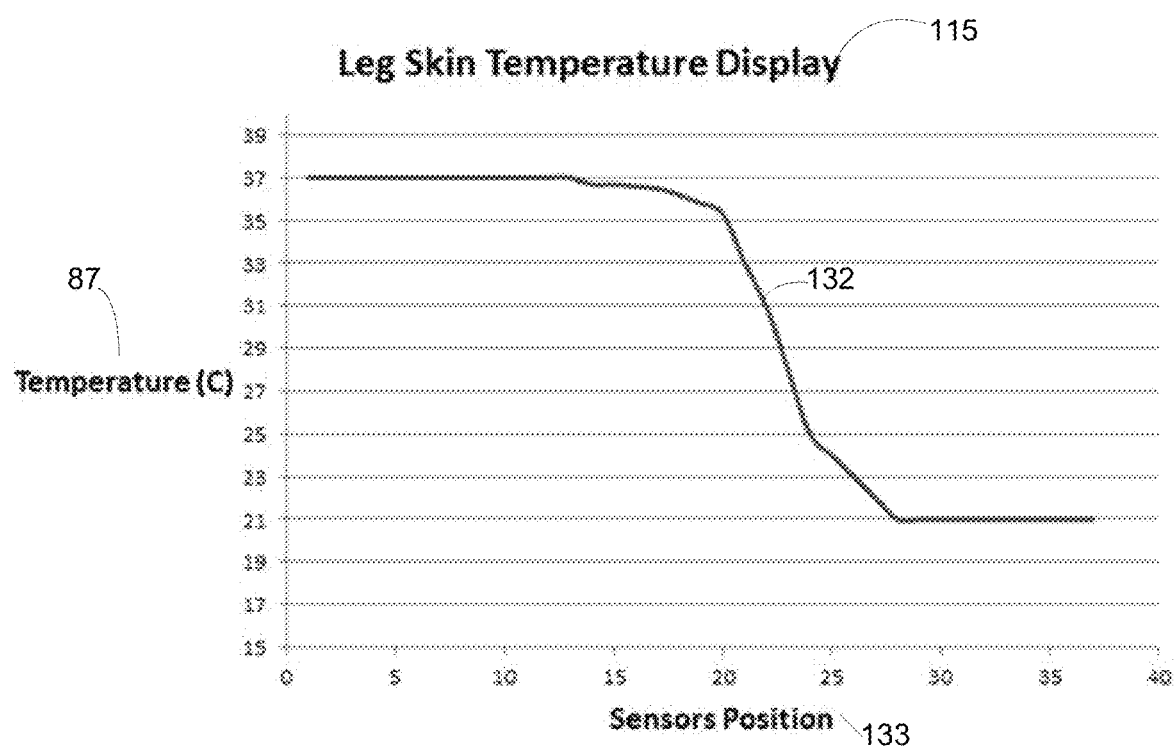
FIG. 1g is an example of a display format for a gradient in which the cardiac performance indicator indicates unhealthy cardiac performance.

FIGS. 1f and 1g illustrate examples of sensor readings 87 displayed graphically in a display format 115 as gradients 132.

The Y-axis in both illustrations pertains to sensor readings 87, and in these two instances, the sensor readings 87 are temperature measurements. The X-axis in both illustrations pertains to a relative position 133 of the sensor components 102. Position #1 pertains to a core location 191 on an appendage 190 while Position #40 pertains to an extremity location 192.

In FIG. 1f the gradient 132 embodying the sensor readings 87 constitutes a straight horizontal line indicating the blood flow at the extremity location 192 is no different than the blood flow at the core location 191. The cardiac performance illustrated in FIG. 1f is that of good health.

In contrast, the cardiac performance illustrated in FIG. 1g is that of poor cardiac performance. The gradient 132 in FIG. 1g slopes significantly downward as the locations 88 get further and further from the core location 191. The differences between the core location 191 and the extremity location 192 are severe.

II. Alternative Embodiments

No patent application can disclose all of the potential embodiments of an invention. In accordance with the provisions of the patent statutes, the principles and modes of operation of the apparatus are explained and illustrated in certain preferred embodiments. However, it must be understood that the apparatus may be practiced otherwise than is specifically explained and illustrated without departing from its spirit or scope.

The description of the apparatus provided below should be understood to include all novel and non-obvious combination of elements described herein, and claims may be presented in this or a later application to any novel non-obvious combination of these elements. Moreover, the foregoing embodiments are illustrative, and no single feature or element is essential to all possible combinations that may be claimed in this or a later application.

III. Detailed Description of Apparatus and Components

Figure 2:
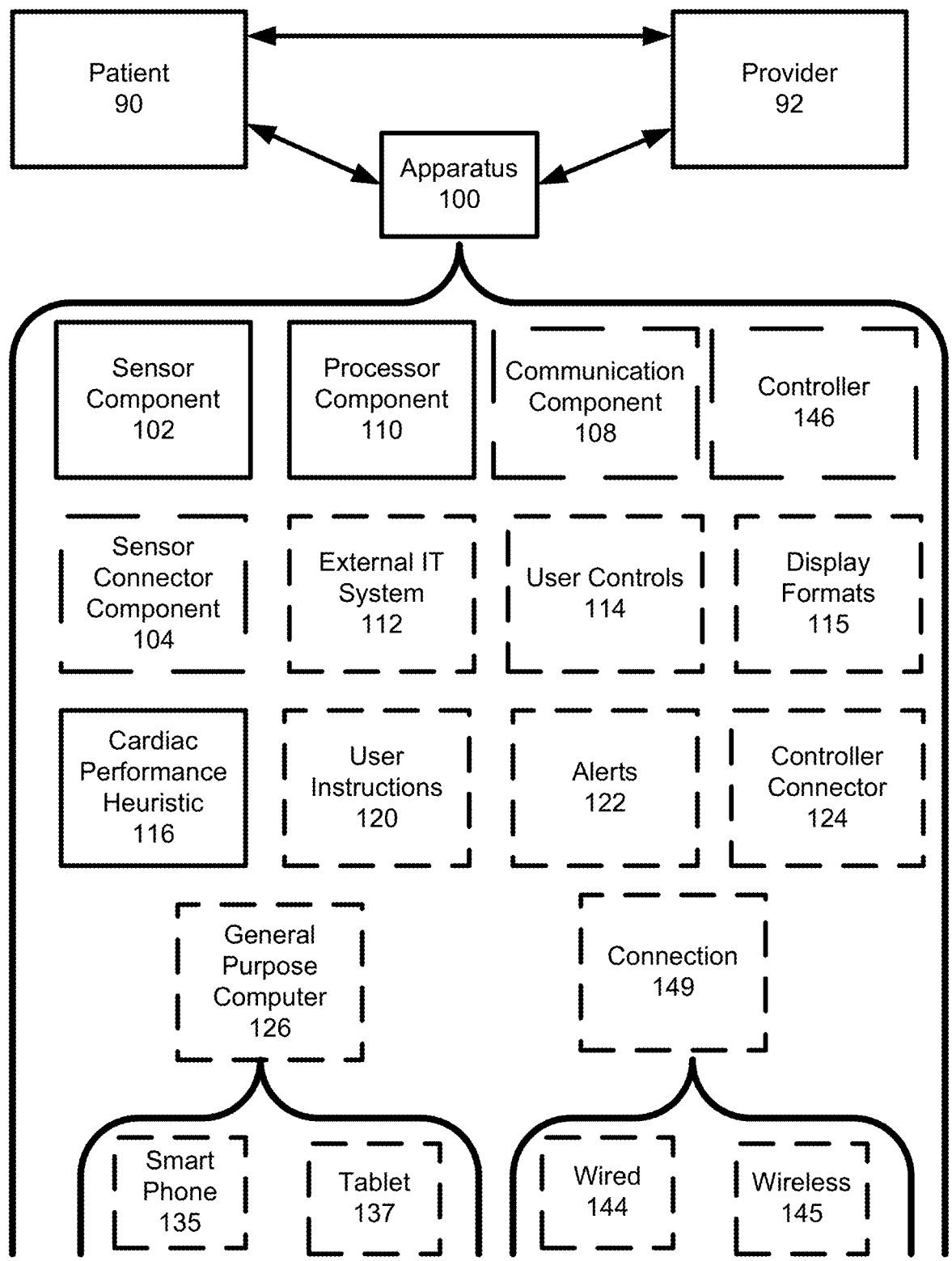
FIG. 2 is a block diagram illustrating an example of interaction between a patient and healthcare provider using the apparatus, and some of the different components and data elements that can be involved in the functionality of the apparatus.

FIG. 2 is a block diagram illustrating an example of some of the different components and data elements that can be involved in the functionality of the apparatus 100. The apparatus 100 can be comprised of a wide variety of different components and involve a wide variety of different types of data. Optional components are indicated by the presence of dotted lines.

A. Apparatus

The apparatus 100 can be used in a variety of different contexts, but is typically used as part of a broader set of interactions between the patient 90 and the provider 92. As indicated by the various arrows in FIG. 2, the apparatus 100 can directly interact with both the patients 90 and providers 92. For example, the apparatus 100 can be positioned on the patient 90 (typically on an appendage 190 such as a leg or arm) to capture readings 87 from the patient 90. The apparatus 100 can provide the resulting information to the providers 92 in a variety of different ways.

The original inspiration for the apparatus 100 was to proactively identify circulatory problems by looking for differences in temperature at different locations 88 on a patient 90. Temperature measurements can be evaluated in a variety of different ways, including but not limited to changes in temperature over time, singular instances of temperature below a certain threshold value 134 (i.e. abnormal temperature), and/or hybrid approaches thereof. By way of example, if the temperature drops at a certain point in the leg or arm of a patient 90, there could be a circulatory problem at that location 88 that needs to be investigated and addressed.

Different embodiments of the apparatus 100 can involve different configurations of components. For example, in some embodiments the apparatus 100 can be used to identify a temperature gradient 132 while in another embodiment some other metric is the focal point of attention. In still other embodiments, entire arrays of different patient attributes 85 (including specific combinations of attributes) can serve as the focal point for the capture of data by sensor components 102. Processing by the apparatus 100 can utilize potentially any raw sensor measurement as well as any metric that can be derived from a raw sensor measurement. In some embodiments of the apparatus 100, the apparatus can access inputs for processing data that are captured by applications or systems outside the apparatus.

Different embodiments of the apparatus 100 can involve different degrees of automated processing that are triggered by the sensor data captured by the apparatus 100. For example, processing of the captured sensor measurements could be limited to simply displaying the data in some embodiments of the apparatus 100. In other embodiments, various heuristics 116 can be performed by a processor in the apparatus 100 itself or by other instrumentation downstream from the apparatus 100. For example, the apparatus 100 could be configured to provide certain notifications in certain contexts to providers 92 and patients 90 alike. The wide variety of different triggering events for such automated notifications can be as virtually limitless as the different types of data that can be useful to the monitoring and treatment of patients 90.

The apparatus 100 can be used in a variety of different contexts, including an emergency room (ER), an intensive care unit (ICU), a critical care unit (CCU), surgical recovery, other hospital settings, ambulances, nursing care facilities, physician offices, and the homes of patients 90.

B. Sensor Component

The apparatus 100 can use multiple sensor components 102. The apparatus 100 can incorporate a wide variety of different sensor components 102 with a wide variety of different sensor attributes.

a. Type of Measurement

Sensor components 102 can vary widely in terms of the type of data that is captured. Temperature is a common example of a type of data that can be captured by sensor components 102 incorporated into the apparatus 100. In alternative embodiments, other types of sensor components 102 can be used. In some embodiments of the apparatus 100, a wide variety of different types of sensor components 102 can be incorporated into the apparatus 100.

Figure 4:
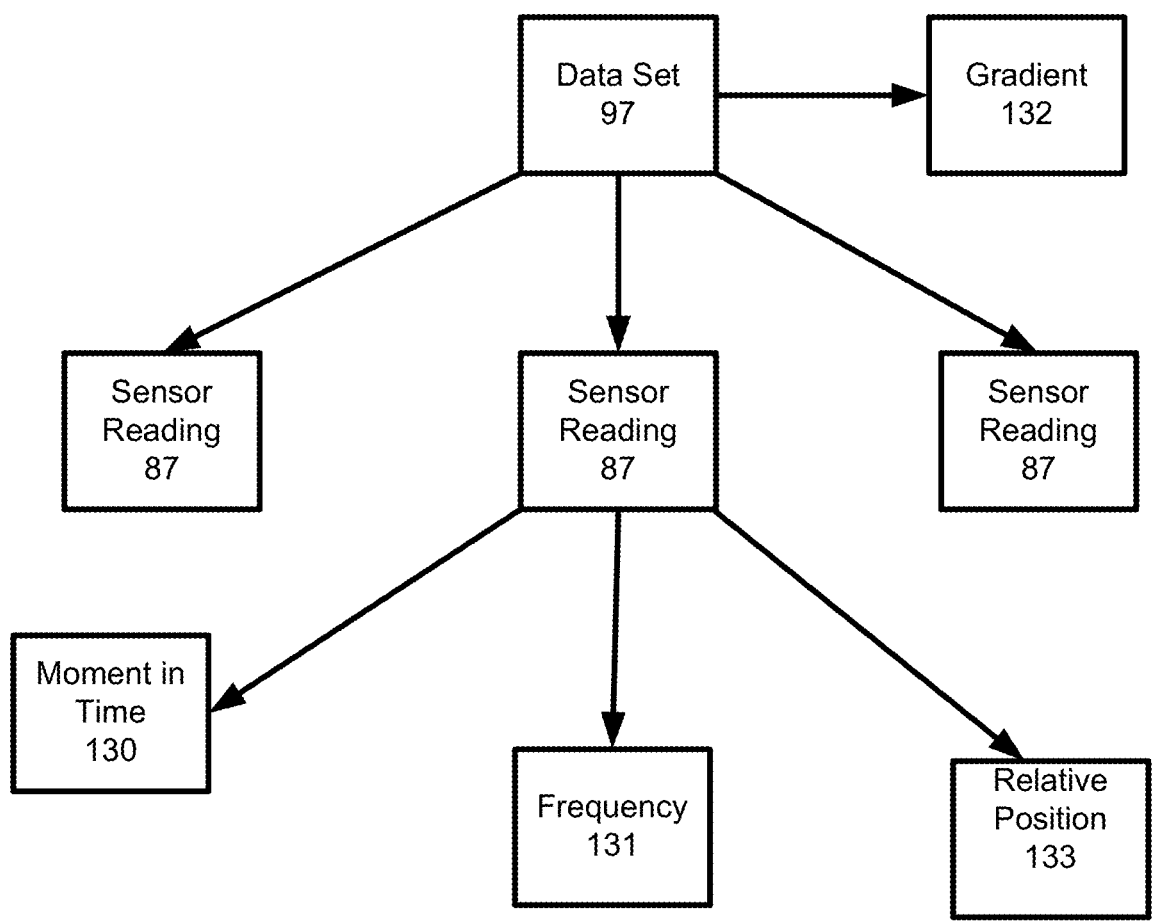
FIG. 4 is a data diagram illustrating the relationships between a data set, the sensor readings that can make up a data set, and some of the attributes that can relate to a sensor reading.

As illustrated in FIG. 3a, sensor components 102 can measure oxygen saturation, electricity conductivity, pH levels, temperature and potentially other phenomenon. As illustrated in FIG. 4, a sensor reading 87 captured by a sensor can also include information relating to a moment in time 130, frequency 131, and a relative position 133 of the sensor component 102 with respect to other sensor components 102.

b. Frequency

Some sensor components 102 can capture sensor readings 87 on a continuous basis. Other sensor components 102 can be configured to capture sensor readings 87 at a specific frequency. In some embodiments of the apparatus 100, the frequency 131 of sensor readings 87 can be automatically adjusted by programming logic in the apparatus 100 that is selectively influenced by relevant attributes pertaining to the patient 90, the sensor component 102, and/or other factors.

c. Locations and/or Relative Positions

In some embodiments of the apparatus 100, it may be important for the apparatus 100 to know the precise location 88 of a particular sensor component 102 with respect to the body of the patient 90. In other embodiments, the relative position 133 of a particular sensor component 102 with respect to other sensor components 102 is all that is required. For example, in the sensor-strip 142 embodiment of the apparatus 100 illustrated FIG. 5a, all that is needed is the relative position of each sensor component 102 in order to generate the data displays as illustrated in FIGS. 1f and 1g.

C. Sensor Connector Component

Returning to FIG. 2, the apparatus 100 can include a sensor connector component 104, such as a sensor strip 142 that encompasses and/or includes the various sensors 102. In other embodiments of the apparatus 100, the sensor connector component 104 is virtually any structure or mechanical configuration that is used to secure the position of the sensor components 104.

D. Processor Component

The processor component 110 is the device the performs the processing logic of the apparatus 100. The range of processing performed by the apparatus 100 can be as basic supporting the electronic display of sensor readings 87 to the performance of advanced cardiac performance heuristics 116 that can selectively create cardiac performance indicators 89 based on a wide range of different inputs (see FIG. 1e).

Computing power can be used to transform the apparatus 100 from a mere reporting device to a device that can be configured to address certain conditions and operating parameters. In some embodiments of the apparatus 100, the processor component 110 has the capacity of function as a general purpose computer 126, i.e. possesses the ability to run software, install updates, and store data. In some embodiments of the apparatus 100, the processor component 110 can be a general purpose computer 126 that is connected to (see FIG. 5b) or in communication with (see FIG. 5c) the sensor components 102. The apparatus 100 can be implemented in such a manner as to allow users to interact with the apparatus 100 through a smart phone 135, tablet 137, or other similar general purpose computer 126.

In some embodiments, the processor component 110 will be the same device as the communications component 110, such as a controller 146 and it will include: a variety of user controls 114; the ability invoke various heuristics 116; the ability to create, store and submit user instructions 120; the ability to create an automated alert 122; and the ability to export output data to external systems and applications such as external IT systems 112.

E. Communication Components and Controllers

A communication component 108 is potentially any mechanism or structure that can communicate data captured by the sensor components 102 and communicate that information to the provider 92, the patient 90, and/or other devices. In many instances, the communication component 108 will include some type of visual display such as a display screen 147. The communication component 108 may also include audio or even tactile capabilities.

One common category of communication component 108 is a controller 146. A controller 146 provides two way communications with the apparatus 100, meaning that the controller 146 can both send and receive information from the apparatus 100.

Some embodiments of the apparatus 100 can involve communication components 108 specially dedicated to providing the functionality of the apparatus 100. For example, a controller 146 can be permanently attached to a sensor strip 142 and serve no purpose outside of the functionality of the apparatus 100. In other embodiments, the apparatus 100 can utilize a general purpose computer 126, a laptop computer, a tablet computer 137, a smart phone 135, or some other non-dedicated device to provide the functionality of the communication component 108.

Figure 5A:
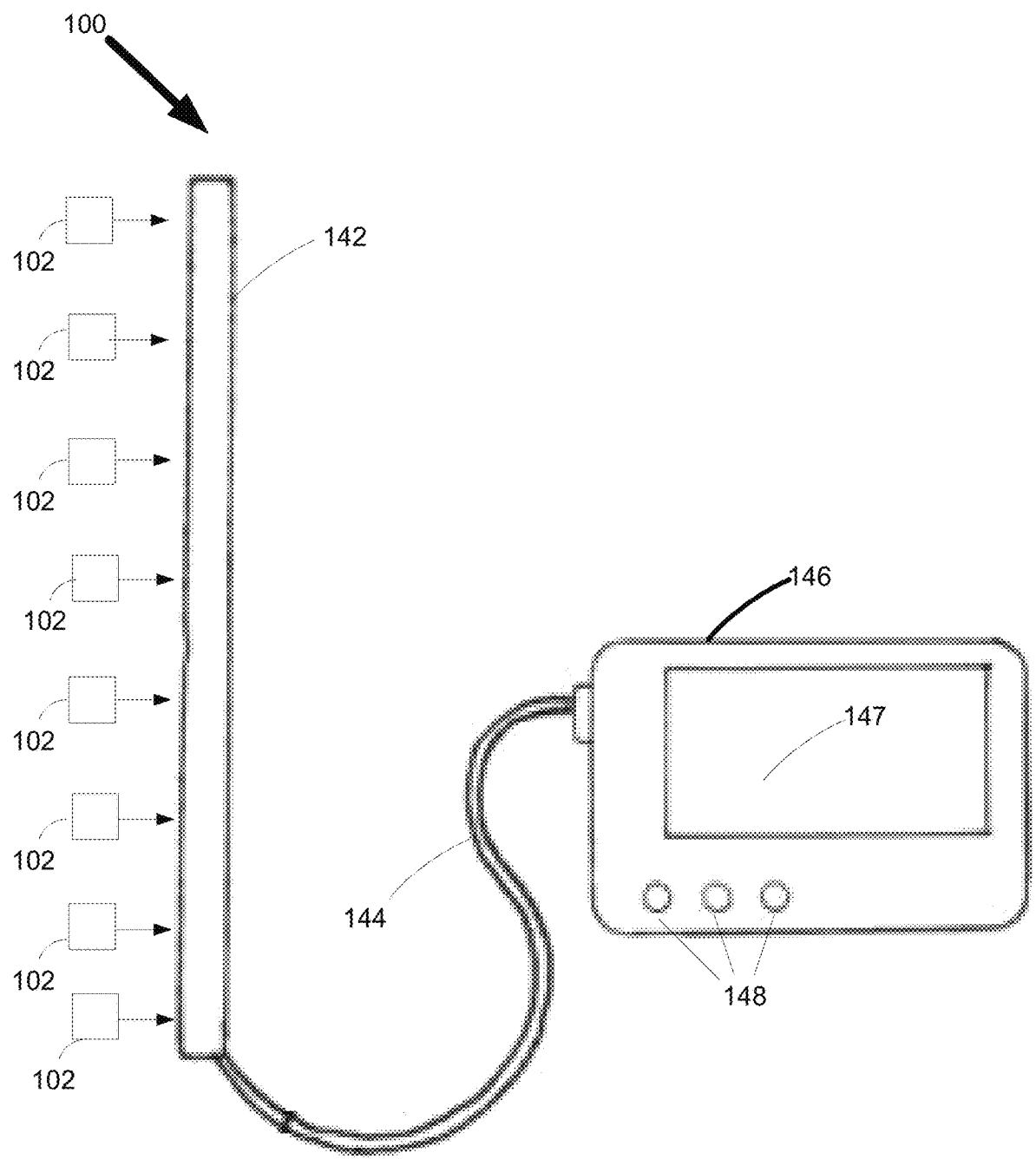
FIG. 5a is diagram illustrating an example of an apparatus that has a dedicated special purpose controller attached.

In the example of the sensor strip 142 embodiment of the apparatus 100 illustrated in FIG. 5a, the display component 108 is a dedicated controller 146 that includes the ability to not only display information, but to also configure the display of information as well as provide instructions to the sensor components 102 and the apparatus 100 generally.

F. User Controls

A user control 114 is either a physical or virtual mechanism by which a user such as a provider 92 or patient 90 can provide an instruction 120 to the apparatus 100. For example, a user control 114 can be used to define the criteria for triggering an alert 122, changing a display format 115, or some other action. In some embodiments, user controls 114 are found in an interfacing device, such as a smart phone 135, tablet computer 137, laptop computer, desktop computer, etc. Examples of user controls 114 include but are not limited to buttons 148, knobs, dials, display screens 147 that are touch screens, keyboards, joysticks, voice recognition technology, light pens, mice, and other commonly known information technology devices for human-machine interactions.

User controls 114 can impact both the inputs and outputs of the apparatus 100.

G. Display Formats

Returning to FIG. 2, different embodiments of the apparatus 100 have the ability to provide different capacities with respect to display formats 115. In some embodiments, the display formats 115 are fixed, and are not subject to configuration by any user. In other embodiments, a user such as a provider 92 or even a patient 90 can use a user control 114 to configure the display formats 115 used by the communication component 108. FIGS. 1f and 1g are examples of display formats 115 that involve graphs of gradients 132.

H. Cardiac Performance Heuristics

A cardiac performance heuristic 116 is a predefined process (that is subject to dynamic configuration in some embodiments) that can be created, stored, and automatically invoked in response to a set of triggering criteria. The heuristic 116 can be designed to identify certain follow-up actions in response to certain situations. For example, an alert 122 to a provider 92, a patient 90, or even the family member of a patient 90 can be automatically sent out when triggered by certain sensor measurements and/or other relevant conditions.

As illustrated in FIG. 1e, it is the cardiac performance heuristic 116 that determines what are the inputs and outputs of the apparatus 100.

I. User Instructions

A user instruction 120 is a means by which a user of the apparatus 100 can influence the functionality of the apparatus 100. Different embodiments of the apparatus 100 can possess a different range of configurable options, with some embodiments providing absolutely no capacity to receive user instructions 120. User instructions 120 can impact the functionality of the apparatus 100 in both substantive as well as presentation-related ways.

J. Alerts

An alert 122 is a communication generated by the apparatus 100 to convey information. The different recipients of a particular alert 122 can be determined by the applicable instruction 120 setting up the alert 122. Alerts 122 can be transmitted in the immediate physical presence of the apparatus 100, as well as via e-mail, text message, automated phone calls, social media, etc. In different embodiments of the apparatus 100, different individuals can be authorized to define alerts 122. Security rules can prevent undesirable occurrences, such as for example preventing the overriding of a doctor-defined alert by a member of the patient's family.

K. External IT Systems

Any information technology system external to the apparatus 100 is a potential partner of the apparatus 100 with respect to information sharing. Data from external IT systems 112 can be used to improve the derivation of the cardiac performance indicator 89. For example, external IT systems 112 can include patient-specific medical information such as age, medical history, etc. that can impact how sensor readings 87 are interpreted. In addition to providing data inputs to the apparatus 100, external IT systems 112 can also receive inputs from the apparatus 100. For example sensor readings 87 and cardiac performance indicators 89 can be automatically added to a patient's medical records. Information relating to a patient's cardiac performance can impact external devices that may benefit from that knowledge.

The apparatus 100 can be implemented to support comprehensive data integration by external IT systems 112 that are both broad and comprehensive in scope.

L. Controller Connector and General Purpose Computers

Figure 5B:
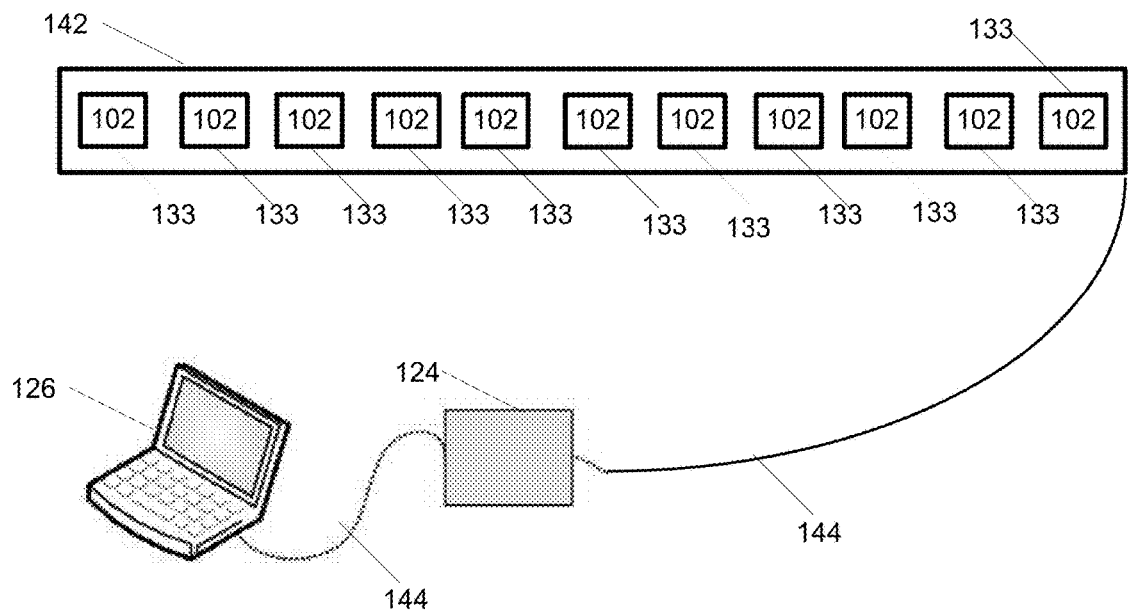
FIG. 5b is a diagram illustrating an example of an apparatus that uses a interface device to connect a general purpose computer to the apparatus.
Figure 5C:
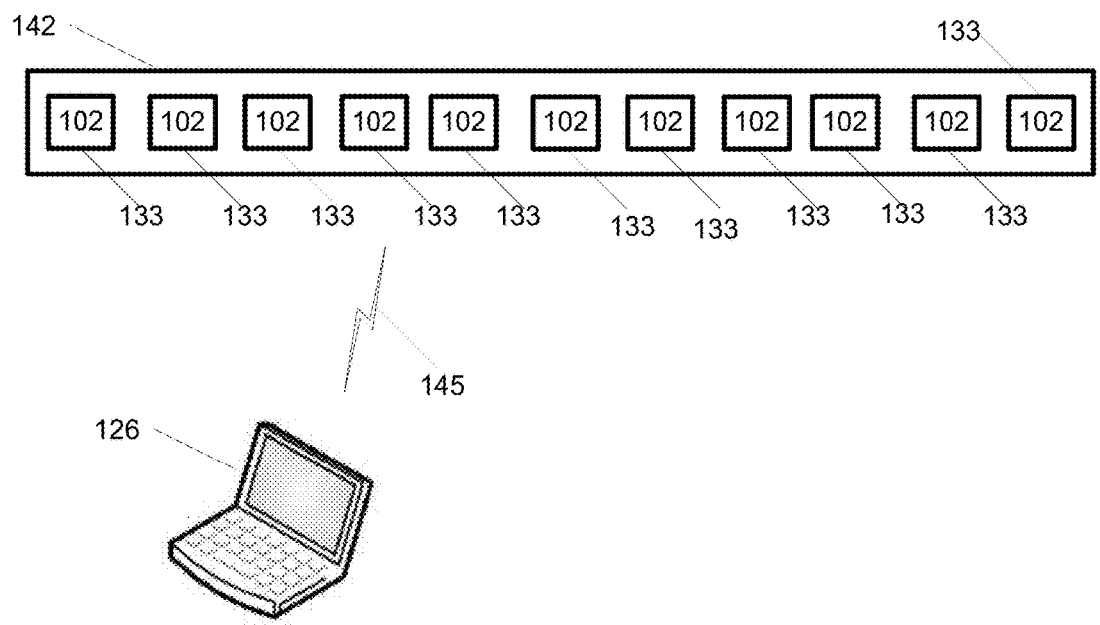
FIG. 5c is a diagram illustrating an example of an apparatus that can interact with a general purpose computer without the inclusion of an interface device.

A controller connector 124 can be a device physically separate from the other components of the apparatus 100 or it can be integrated into other components, such as a sensor strip. A controller connector 124 allows for the apparatus 100 to interact with general purpose computers 126 such as smart phones 135, tablets 137, laptop computers, and other types of computers to allow users to both receive and submit information to the apparatus 100. This is beneficial for a wide variety of reasons. Specially dedicated interface devices can constitute a needless expense, and many users are more familiar with the user interfaces on their general purpose computer 126. A controller connector 124 provides for using general purpose devices to support the functionality of the apparatus 100. The keyboards, display screens 147, speakers, buttons 148, and other capabilities of the general purpose computer 126 can become temporary components of the apparatus 100. FIGS. 5b and 5c illustrate different examples of such temporary integration.

M. Connections

A connection 149 is virtually any mechanism by which information can be exchanged between components in the apparatus 100, or from the apparatus 100 to the outside world. The apparatus 100 can incorporate both wired connections 144 as well as wireless connections 145. In different contexts, different design choices can be honored while implementing the apparatus 100.

IV. Detailed Description of Sensors

Sensor components 102 are the primary component for the apparatus 100 for the gathering of information used by the apparatus 100 to generate an assessment of a patient's cardiac performance (i.e. cardiac performance indicator 89).

A. Variations of Sensor Components

FIG. 3a is a hierarchy diagram illustrating an example of different categories of sensor components 102 that can be included in different embodiments of the apparatus 100. FIG. 3a illustrates different types of sensor components 102 based on the type of information captured by the sensor component 102. As illustrated in FIG. 3a, sensor components 102 can utilize oxygen saturation sensors 136, electricity conductivity sensors 138, pH sensors 139, and temperature sensors 140. Other types of non-invasive sensors that can capture meaningful information when positioned on the skin of the patient 90 can be used as sensor components 102 for the apparatus.

Sensor components 102 can also vary widely in terms of their structural configuration. They can also use different techniques and components for being securely positioned on the patient 90. Some sensor components 102 can be integrated with other components of the apparatus 100 such as processor components 110 and communication components 108, as well as the specific connections 149 (whether wired 144 or wireless 145) that are used.

B. Example of Sensor Component in a Subassembly

Figure 3B:
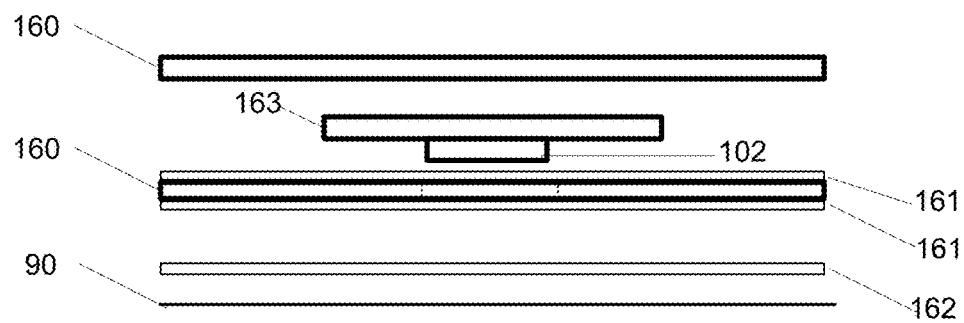
FIG. 3b is a side view diagram illustrating an example of a sensor component and some accompany components that can provide for securing the sensor component on a patient location.

FIG. 3b is a side view diagram illustrating an example of a sensor component and some accompany components that can provide for securing the sensor component on a patient location. The sensor component 102 is mounted to a circuit board 163. The circuit board 163 may include its own communication component 108 or even its own processor component 110. The circuit board 163 and attached sensor component 102 are sandwiched between layers of foam 160. Adhesive layers 161 are disbursed at various locations within the subassembly to keep the various components integral to each other. A peel away layer 162 is positioned at the bottom of the subassembly, providing users with the ability to remove the peel away layer 162, exposing the lowest adhesive layer 161 to come into contact with the skin of the patient 90. This provides for the securing of the sensor component 102 with respect to a particular location 88 on the patient 90.

Different embodiments of the sensor component 102 can involve different subassembly configurations. Sensor components 102 can be physically attached to each other in some embodiments, while using wired connections 144 in other embodiments. In some embodiments, sensor components 102 will each possess their own means for being securely positioned on the patient 90, while in other embodiments such functionality will reside in a strip 142 or some other form of sensor connector component 104.

C. Sensor Connector Components

Figure 3C:
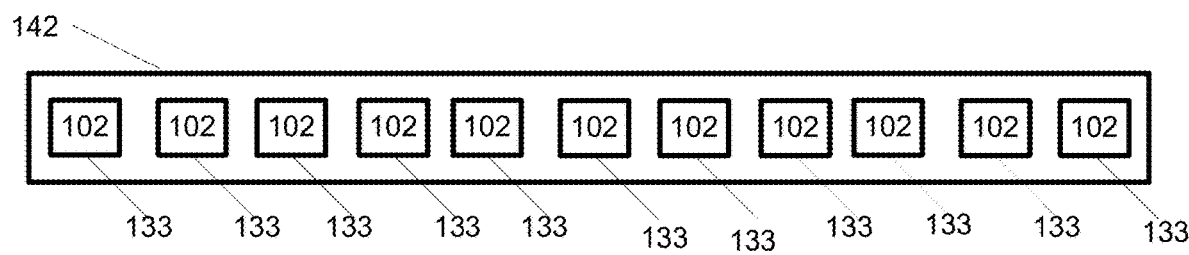
FIG. 3c is a block diagram illustrating an example of a sensor strip.

FIG. 3c is a block diagram illustrating an example of a sensor strip 142 that includes 11 securely positioned sensor components 102 in 11 relative positions 133. In many embodiments of the apparatus 100, there will be a relatively high number of sensor components 102. In such instances, having some physical connection mechanism (a sensor connector component 104 such as a sensor strip 142) is highly desirable. It is far easier to grab a single strip 142 by the hand than it is to grab 20 or 30 sensor components 102 that are not attached to anything else. Moreover, the sensor strip 142 also has the advantage of securing each sensor component 102 in a relative position 133 with respect to the other sensor components 102 on the strip 142.

By having strip 142 securely position multiple sensor components 102 into a single file sequence of sensor components 102, the strip 142 of FIG. 3c is both easier to handle, and can readily generate output such as the gradients 132 displayed in FIGS. 1f and 1g.

V. Cardiac Performance Heuristics and Indicators

At the heart of the apparatus 100, is the capability to generate a cardiac performance indicator 89.

A. Inputs—Different Heuristics Utilize Different Factors

FIG. 1e is an input-output diagram illustrating an example of the different inputs and outputs that can be involved in the functionality of the apparatus 100. Different embodiments of the apparatus 100 can also give different weight to different inputs. For example, a user instruction 120 from a provider 92 or medical history information from an external IT system 112 may suggest that a particular patient 90 is particularly vulnerable to cardiovascular problems, and as such, the cardiac performance indicators 89 can be correspondingly adjusted with alerts 122 being triggered in that instance when they would not be triggered for other patients 90 in otherwise identical circumstances.

The apparatus 100 can also utilize some inputs to counteract potential measurement errors with respect to other inputs. By way of example, in the context of temperature sensors 140 it may be desirable for the sensors 140 to also capture ambient temperature measurements 141 to factor in for erroneous sensor readings 87 resulting from differences in insulation for different sensors 140. The upper part of the strip 142 can be covered so as to form an insulation barrier over the sensor 140.

Further down the strip 142 may not covered and may not have an insulation barrier. The apparatus 100 may measure a gradient 132 along the strip due to the different ambient conditions. This could possibly be a false positive reading. If the sensor 140 can measure both the skin temperature reading 87 and a related ambient reading 141, then the processor component 110 of the apparatus 100 can normalize the reading 78, or use a correction factor when utilizing the reading. Thus differences in the physical configuration of the sensors 140 can merit differences in the treatment of input variables.

Given the number of potential input parameters for the cardiac performance heuristics 116, it is not possible to graphically illustrate all of the combinations or to use text to illustrate how a difference with respect to a single input can selectively impact the output of the apparatus 100.

B. Data—Different Levels of Data and Analysis

FIG. 4 is a data diagram illustrating the relationships between a data set 97, the sensor readings 87 that can make up a data set 97, and some of the attributes that can relate to a sensor reading 87 such as time 130, frequency 131, and relative position 133. The apparatus 100 and the cardiac performance heuristics 116 that support the functionality of creating cardiac performance indicators 89 can be configured and even customized in a wide variety of different ways.

Different embodiments of the cardiac performance heuristics 116 can evaluate and compare data at different levels and in different groupings. A data set 97 can include potentially multiple sensor readings 87 from multiple sensor components 102. Comparative analysis is a highly useful tool in looking for evidence of poor cardiac performance. See FIG. 1g. Returning to FIG. 4, a data set 97 can correlate to a gradient 132. Composite data sets 132 can include more than one gradient 132. A single gradient 132 can include multiple sensor readings 87. A single sensor reading 87 can be associated with a specific moment in time 130, a specific frequency 131, and a specific relative position 133.

Just as the cardiac performance heuristic 116 can be implemented in a wide variety of different ways to give different weights to different inputs, the heuristic 116 can also be implemented to operate at different levels of data. Some embodiments of the heuristic can factor in data from multiple data sets 97 while other embodiments can focus exclusively on data from a single apparatus 100 used at a single moment in time 130.

C. Outputs—Cardiac Performance in a Human Being

The human body is a collection of organ systems working together to perform the tasks and meet the needs of the body. Most organ systems work on "as needed" basis and have a less active or dormant state when not needed. Even organs such as the brain and heart which are never truly dormant vary from levels of high activity to levels of substantially lower activity. All organ systems require a blood supply. Blood provides oxygen, nutrients and enzymes. It also carries away cellular metabolic waste products.

An adult human body has approximately five liters of blood. Interestingly, this volume is many times less than the volume the vascular system. This is because while some organs are in a high activity state, other organs are in a less active or dormant state. Therefore, the body continuously directs blood flow to organs that need it and reduces blood flow to inactive organs because there is not enough blood volume to supply all organ systems with maximum blood flow at the same time. For example, during exercise or physical activity the skeletal muscular system requires higher amounts of blood. Conversely, during rest or sleep blood supply to skeletal muscles is reduced because they have less blood supply demand.

Blood flow is managed by the vascular system. The arteries and veins of the vascular system can expand or contract, which is called vasodilation or vasoconstriction, respectively. Vasodilation and vasoconstriction are key components for managing blood flow. At the center of the vascular system is a heart that is responsible for pumping blood throughout the vascular system.

Arteries will vasodilate to allow more blood flow to an organ. They will vasconstrict to reduce blood flow. Systemic vascular resistance (SVR) is a term used to describe the level of vasodilation or vasoconstriction. SVR is a concept that can be expressed mathematically as a numerical value, a systemic vascular resistance value 93. Vasdilation is a level of lower systemic vascular resistance. Vasoconstriction is a higher level.

Vasodilation=↓ decreased Systemic Vascular Resistance

Vasoconstriction=↑ increased Systemic Vascular Resistance

The brain, heart, lungs, liver and kidney are vital organs. Their performance is essential for life, hence their designation as vital. Maintaining blood supply to these organs, even small amounts of blood, is extremely important. If the balance of all organ systems is disrupted for any reason, the body will work toward supplying at least the minimum amount of blood supply to the vital organs. This balance can be changed by many causes.

If a body experiences certain types of trauma or if it is in an aged or diseased state, the cardiovascular organ system could be hindered which changes the balance of all organ systems. If there is trauma resulting in significant blood loss, this could adversely affect the cardiovascular system. Age diminishes all organ systems, including the cardiovascular system. Certain types of diseases such as coronary artery disease or cardiomyopathy affect the heart, which affects the cardiovascular system. Performance of the cardiovascular system is measured by cardiac output. Trauma, age and disease can cause reduced cardiac output. Reduced cardiac output means less blood supply to all organs, including the vital organs. A natural physiologic response to reduced blood supply is to increase systemic vascular resistance to non-vital organs in order to preserve blood supply for vital organs.

The relationship between a cardiac output estimate 95 and a systemic vascular resistance value is shown in the equation below.

Cardiac Output=Systemic Vascular Resistance+Mean Arterial Pressure

Mean arterial pressure is directly and easily measured using a blood pressure cuff. Cardiac output and systemic vascular resistance are not easily measured. Cardiac output can be directly measured by inserting a Swan-Ganz catheter into the pulmonary artery and making a thermal dilution measurement. This provides accurate real-time measurement of cardiac output, which is very valuable. The Swan-Ganz catheter must be indwelling, which means it must remain inserted in the pulmonary artery, to provide continuous measurement. Indwelling catheters can be difficult to maintain. They are susceptible to infection. The decision to use a Swan-Ganz catheter for continuous monitoring of cardiac output must be based on the risk associated with indwelling catheters.

Providers 92 treating patients with extreme trauma or severe disease states will monitor vital signs. It is very desirable to know the cardiac output estimate 95. This information helps guide and assess treatment of the patient 90. A device that could non-invasively monitor cardiac output accurately and continuously would be valuable. The apparatus 100 is such a device.

Reduced cardiac output leads to increased systemic vascular resistance for non-vital organs, which means less blood supply to these organs. Blood supply will be reduced to the extremities, meaning the arms and legs. If cardiac output is reduced by only a small amount, blood supply will only be reduced to the far ends of the extremities, which are the hands and feet. If reduction is more severe, blood supply will be reduced to more portions of the extremities.

Reduced blood supply to the extremities will result in decreased dermal temperature, which is skin temperature. Depending on the level of cardiac output, a temperature gradient may develop from the top-to-bottom of the extremity. For example, the upper and mid portion of the thigh may be at or near normal temperature, but the calf and foot may be colder. Therefore, monitoring skin temperature may be a valuable way to non-invasively monitor cardiac output.

Blood supplies many things to organs. Heat is one example of what blood can supply. Hence, skin temperature can be a non-invasive monitor of cardiac performance. Oxygen is present in blood. Dermal oxygen saturation levels may also serve as a way to monitor cardiac output. If an 0.2 saturation gradient is measured along the length of an extremity, it may indicate changes in cardiac output. Other blood or dermal parameters may also be monitored to indicate cardiac performance, such as pH levels or electrical properties like conductivity or resistance.

VI. Variations in Communication Components

As discussed above, the communication component 108 is the means by which information such as a cardiac performance indicator 89 is communicated to the provider 92. A controller 146 is a communication component 108 that is capable of both sending information from a user as well as transmitting information to the user. Different embodiments of the apparatus 100 can involve communication components that are specially dedicated and even permanently attached to the sensor components 102. Other embodiments allow users to temporarily integrate general purpose computers 126 to provide the interface between user and apparatus 100.

A. Permanently Attached and Dedicated Controller

FIG. 5*a* is diagram illustrating an example of an apparatus 100 that has a fully dedicated special purpose controller 146. The controller 146 is not configured to be removed from the sensor strip 142 by users. The apparatus 100 has a sensor strip 142 of eight sensor components 102. The strip 142 is attached to a controller 146 that includes a display screen 147 and several buttons 148. The buttons 148 coupled with a user menu on the display screen 147 can be used to select display formats 115, submit user instructions 120, and provide other types of inputs to the apparatus 100 as discussed above.

B. Wired Controller Connector

FIG. 5*b* is a diagram illustrating an example of an apparatus 100 that uses a wired controller connector 124 (such as a USB cord, a network cable, or some similar type of wired connector 124 to connect a general purpose computer 126 to the sensor components 102 of the apparatus 100. Instead of using a fully dedicated and permanently attached controller 146, FIG. 5*b* illustrates an example of where a user can utilize a general purpose computer that they already have to interact with the sensors components 102.

C. Wireless Controller Connector

FIG. 5*c* is a diagram illustrating an example of an apparatus 100 with sensor components 102 that can interact with a general purpose computer 126 without the inclusion of a controller connector 124. In FIG. 5c, the sensor components 102 themselves can include their own communication capabilities that provide for direct wireless communication with a general purpose computer 126.

VII. Temperature-Based Embodiments of the Apparatus

Although the apparatus 100 can be implemented in a wide variety of different embodiments, the conception of the apparatus 100 was originally inspired to include the use of temperature sensors 140.

A. Process-Flow Views

1. Single Gradient Example

Figures 6A, 6B:
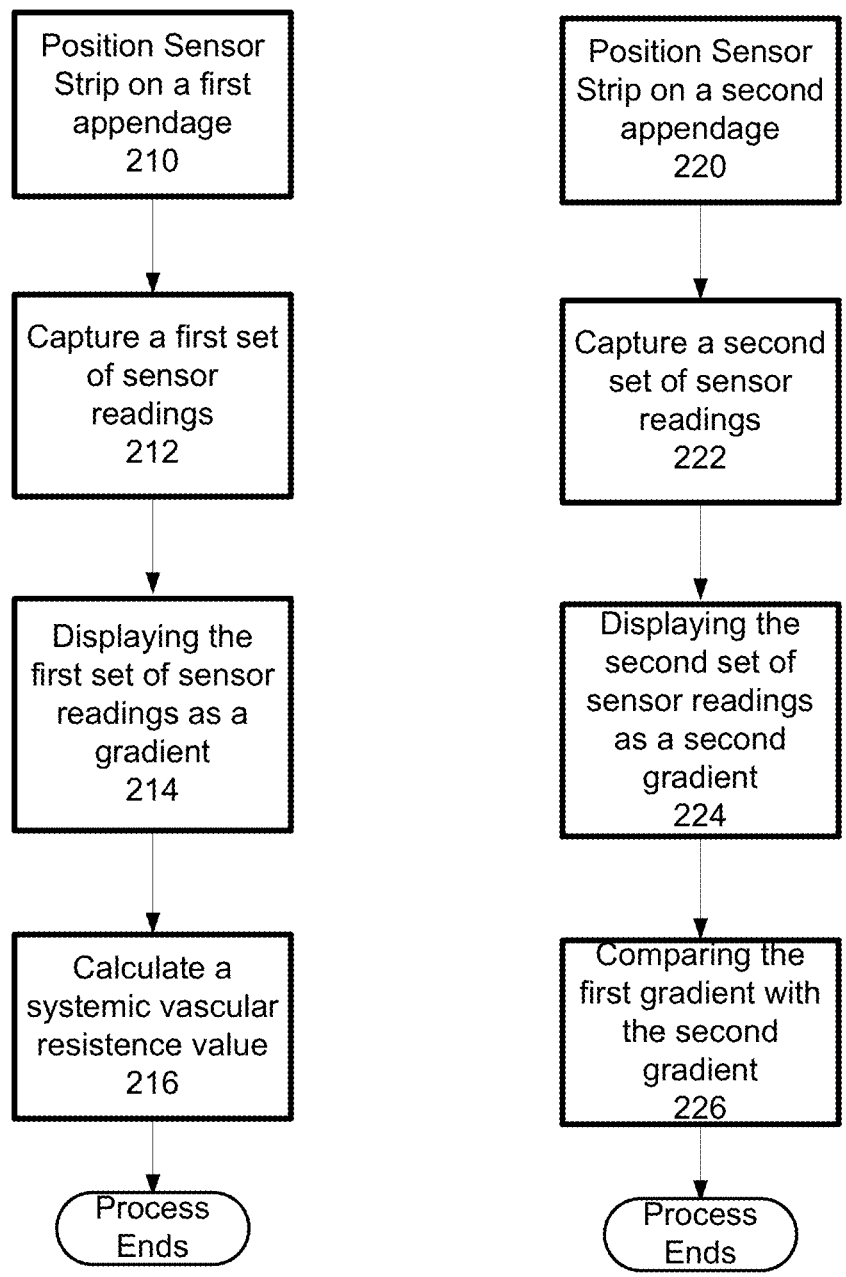
FIG. 6a is a flow chart diagram illustrating an example of a process by which a systemic vascular resistance value is calculated using sensor readings from a temperature sensor.
FIG. 6b is a flow chart diagram illustrating an example of two gradients being compared/contrasted with each other to selectively derive the applicable cardiac performance indicator.

FIG. 6a is a flow chart diagram illustrating an example of a process by which a systemic vascular resistance value 93 is calculated using sensor readings 87 from a temperature sensor 140.

At 210, the sensor strip 142 is positioned on an appendage 190 such as an arm or leg.

At 212, a data set 97 of sensor readings 87 is captured.

At 214, the captured sensor readings 87 are displayed. This display format 115 can be similar to the format illustrated in FIGS. 1f and 1g.

At 216, the systemic vascular resistance value 95 is calculated using the processor component 110. The value 95 can be displayed, compared to a predefined threshold value 134 for the purpose of selecting triggering an alert 122, or put to use in one or more of the ways discussed above.

2. Two Gradient Example

FIG. 6b is a flow chart diagram illustrating an example of two gradients 132 being compared/contrasted with each other to selectively derive the applicable cardiac performance indicator 89.

This process continues with the second gradient 132 after steps 210 through 216 discussed above are performed.

At 220, a sensor strip 142 is positioned on a second appendage 190. This can be the same strip 142 as in step 210 but a different moment of time 130 or it can be a different strip 142 at the same moment of time 130 or at a different moment of time 130.

At 222, a second data set 97 of sensor readings 87 are captured.

At 224, the gradient 132 corresponding to the second data set 97 can be displayed. In some embodiments, it can be helpful to illustrated both gradients 132 simultaneously for comparison purposes.

At 226, the gradients 132 can be compared both visually as well as analytically. As discussed above, the cardiac performance heuristic 116 can be specifically tailored to perform gradient 132 to gradient 132 comparisons for the purposes of generating a cardiac performance indicator 89.

B. Environmental Views/Operating Configurations

Figure 7A:
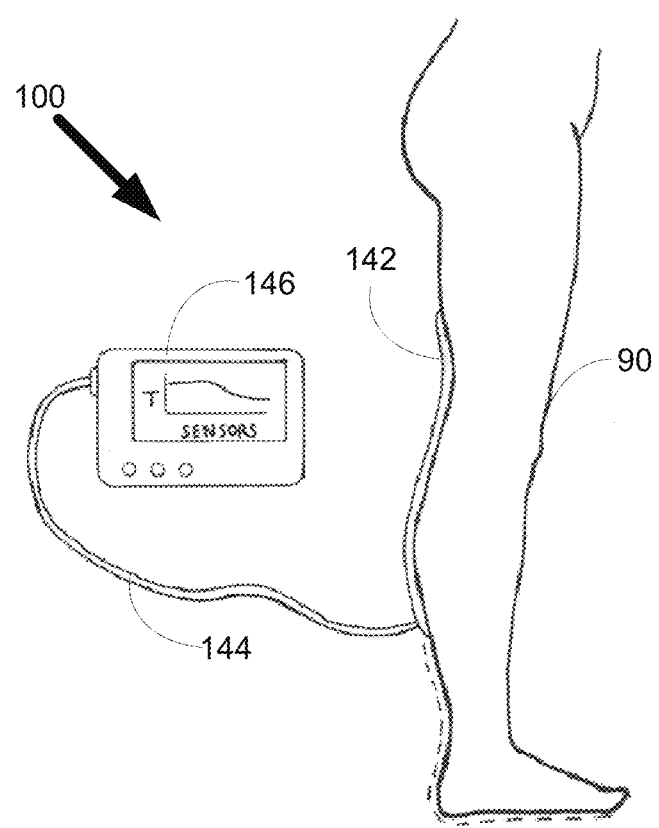
FIG. 7a is an environmental diagram illustrating an example of the apparatus in the context of temperature sensors being positioned on a leg of the patient.
Figure 7B:
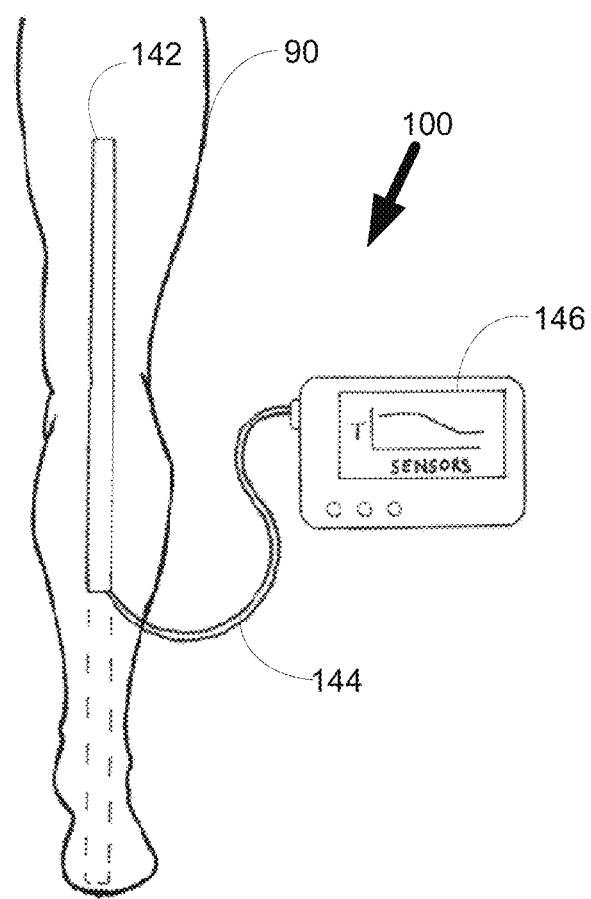
FIG. 7b is an environmental diagram illustrating an example of the apparatus in the context of temperature sensors being positioned on a leg of the patient.

The process flows illustrated in FIGS. 6a and 6b above can be performed in a wide variety of different configurations, including but not limited to the configurations illustrated in FIGS. 7a and 7b.

1. Side View

FIG. 7a is a side view environmental diagram illustrating an example of the apparatus 100 in the context of temperature sensors 140 being positioned on a leg 190 of the patient 90. The temperature sensors 140 are embedded in a sensor strip 142 that is coated with an adhesive layer 161 to facilitate being position on the skin of the patient 90. The controller 146 is attached to the sensor strip 142 through a cord 144 that provides both power and communications to the sensor strip 142.

2. Rear View

FIG. 7b is an environmental diagram illustrating an example of the apparatus 100 in the context of temperature sensors 140 being positioned on a leg 190 of the patient 90. FIG. 7b is a rear view of the illustration in FIG. 7a.

C. Description of Components—Temperature Sensor Apparatus

1. Temperature Sensors

An array of temperature-based sensors 140 (temperature sensors 140) are used in the illustrated sensor-strip embodiment of the apparatus 100. The number of sensors 140 can vary widely. In the context of leg-based applications, it can be desirable to have between about 5-15 sensors for the thigh area, between about 10-20 sensors for the back of the knee, and between about 5-10 sensors for the calf area.

2. Sensor Strip

The array of sensors 140 is housed in a sensor strip 142 that can be securely positioned onto the leg or arm of a patient 90. The senor strip 142 can be designed for positioning from the mid-thigh to mid-calf area, although alternative embodiments can be designed to extend all the way down the backside of the leg.

3. Electrical Cord

The wired connection 144 illustrated in FIGS. 7a and 7b is an electrical cord. Virtually any wired connection 144 or wireless connection 145 can serve as the connection 149 between components 149. However, the use of wired connections 144 helps to keep the apparatus 100 integrated as a single device which can make it easier to deploy as well as store.

4. Controller

A controller 146 is a single device houses the communication component 108 (in the form of a screen 147) and the processor component 110. The controller 146 can provide various user controls 114 (such as a physical button 148 in the housing of the control unit 146) to allow users to change display formats 115. In some embodiments, the control unit 145 can be used to create heuristics 118, submit instructions 120, create automatically invoked alerts 122, and to output data to external IT systems 112.

As discussed above, some embodiments of the apparatus 100 can support a general purpose computer device such as a smart phone 135, tablet computer 137, laptop computer, etc. serving as the controller 146.

D. Detection of SVR

A temperature-based sensor-strip embodiment of the apparatus 100 is designed to detect systemic vascular resistance values 95 in the extremities of the patient 90.

The apparatus 100 will measure the skin temperature of a patient's leg. The apparatus 100 can have the ability to measure temperature at more than one location 88 at the same moment in time 130—with measurements be taken either continuously or periodically over a period of time. The apparatus 100 can continuously measure temperature at all locations and immediately provide measurement information to a processor component 110 that is part of the apparatus 100 (typically housed within the controller 146) and/or to external systems/applications involved in the monitoring of the patient's medical status and in the treating of the patient 90. In many embodiments, a screen 147 on the controller 146 will display all temperature measurements immediately and continuously. Displayed temperature measurements may be in the form of a data plot, with skin location along the X-axis and temperature measurement along the Y-axis. Other data formats 115 can be selected using the buttons 148 on the controller 146 or through other user controls 114. The apparatus 100 can also record measurement information so the information can be reviewed later. Recorded information will include date, time of day and possibly time since recording started. The apparatus 100 may have the capabilities to trigger alerts 122 to indicate particular information, such as temperatures above or below certain limits, variations of temperature between measurement locations or variations of temperature over the time.

The apparatus 100 can include: (1) multiple temperature sensors 140; (2) encompassed in a sensor strip 142; (3) that is connected to controller 146; (4) by a cord 144. The strip 142 of sensors 140 can be attached to the backside (posterior) of a patient's leg. The strip 142 can be long enough to extend from about mid-thigh to mid-calf. The strip 142 can be attached to the patient 90 using adhesive, similar to the way in which a bandage is attached to the skin. Other attachment means are possible. In a preferred embodiment, the apparatus 100 will attach as conveniently as possible so that only one person is needed to attach the strip 142 to the leg, and so that a patient 90 may be able to attach the strip 142 without outside assistance.

The strip 142 of the apparatus 100 can contain a variable number of temperature sensors 140, with that range being between about 24 to 36 temperature sensors 140 in many instances. The strip 142 can be designed to stay on the patient 90 for an extended period of time, maybe as long as about 1 or 2 days. It can be as comfortable as possible for the patient 90 and with a low visual profile. The strip 142 can be designed to insulate it from ambient temperature effects. The strip 142 can be made from biocompatible materials and meet any patient 90 safety needs or skin safety needs. The strip 142 can use a cord 144 (or a wireless network) to connect to a display component 109 such as the controller 146 with a screen 147. The display instrument will display all the temperature measurement information. The screen 147 can display the information immediately and continuously, or as is otherwise desired through the configuration of the controller 146. The controller 146 can be a small device, maybe handheld size or notepad size. In some instances, it will be a general purpose computer, such as a smart phone 135, tablet computer 137, etc. The controller 146 may lie on the bed next to the patient 90, or be attached to the hospital bed. The controller 146 may be battery powered or plug into a wall outlet.

Some embodiments of the apparatus 100 can have the ability to transmit measurement information to other devices, systems, and applications, such as general purpose computers 126 (including tablet computers 137 and smart phones 135) or specialized medical systems.

It is envisioned that the apparatus 100 may be used on other locations of the patient than just the leg. For example, the arm of the patient 90 is another likely location for use of the apparatus 100.

The apparatus 100 can be used to monitor a patient 90 in a wide variety of different contexts. Cardiac output 95 is an important physiologic parameter that is monitored in some patients 90. It is desired to know as quickly as possible if cardiac output starts to decrease. Decreased output can be a serious problem that can lead to cardiogenic shock, which requires immediate medical attention to resuscitate and maintain a patient's life. A physiologic response to decreased cardiac output is to protect vital organs by changing systemic vascular resistance. Vascular resistance of the skin is increased in order to reduce blood flow to the skin. Reduced blood flow to the skin means more blood supply is available to vital organs. Reduced blood flow to the skin also means reduced skin temperature. Therefore, the apparatus 100 can monitor cardiac output by detecting skin temperature changes which are a symptom of changes to systemic vascular resistance. This can be an early warning sign of possible cardiogenic shock and the need for immediate medical attention.

The apparatus 100 can provide this warning by displaying changes in leg skin temperature. Reduced skin blood flow will start at the farthest locations of the extremities, the fingers and the toes. If necessary, reduced flow will continue to progress up the extremities; the arms and legs. The device will be able to display changes in skin temperature. For example, the screen 148 would show normal skin temperature in the thigh region and lower skin temperature in the calf region. If the patient's condition worsens, the screen 148 may show lower than normal temperatures along the entire leg.

The device is envisioned to be used in many different places. It can be used in an emergency room (ER), intensive care unit (ICU), critical care unit (CCU), surgical recovery, elsewhere in a hospital setting, ambulances, nursing care facilities and patient's homes.

It may be possible to monitor other skin parameters that are affected by cardiac output. For example, it is envisioned that this device could measure electrical resistance, ph, chemical or light changes to skin. It may also be possible to implement the apparatus 100 outside the context of skin sensors.

E. Data Display Formats

FIG. 1f is an example of a temperature chart that could be generated by application of a sensor-strip embodiment of the apparatus 100 used on the leg of a relatively healthy patient 90.

The display component 108 of the apparatus 100 can display the temperature measurement. The vertical axis is temperature. The horizontal axis is the relative position 133 of the sensor 140. The first sensor may be the sensor at the patient's mid-thigh. The last sensor may be the sensor at the patient's mid-calf, or alternately their toes. FIG. 1f shows all sensors measuring the same temperature. This would happen if there is no temperature gradient between sensors. This would tell the doctor that the leg skin temperature is uniform from thigh to calf, or thigh to toes.

FIG. 1g is an example of a temperature chart that could be generated by the application of a sensor-strip embodiment of the apparatus used on the leg of a patient with circulatory problems.

FIG. 1g shows a temperature gradient between the temperature sensors 140. The sensors 140 in the thigh area, sensors 1-12, all display the same temperature of 37° C. The sensors 140 in the middle area across the back of the knee, sensors 13-27, display a consistent decrease in temperature. The last sensors 140 in the calf area, sensors 28-36, show a consistent low temperature of 21° C. The gradient shown above results from the leg skin being at different temperatures. This may result from the patient's body responding to a decrease in cardiac output. The body responds by increasing systemic vascular resistance (SVR). Increased SVR means less blood flow to peripheral areas, such as arms and legs. Less blood flow in arms or legs can be detected by skin temperature gradient.

Different embodiments of the apparatus 100 can trigger different alerts 122 based on the magnitude of the temperature gradient indicated in the display, changes in temperature over time, or a temperature measurement falling outside a predefined safe range. Such settings can also be customized to factor in other attributes related to the patient 90. In some embodiments, providers 92 can customize the triggering criteria for an alert 122 to include data supplied to the apparatus 100 that does not originate from the sensors 140 within the apparatus 100.

VIII. Index of Elements

Table 1 below provides an index of element names and element numbers.

TABLE 1

| Element Number | Element Name | Description |
|---|---|---|
| 85 | Patient Attribute | Potentially any attribute of the patient 90 that can be relevant for the purposes of assessing the cardiac performance of a patient 90 and that can be captured in the form of a sensor reading 87 by a sensor component 102. Examples of potentially relevant patient attributes 85 can include skin temperature, pH level, electrical conductivity, oxygen saturation and other attributes that can be either directly or indirectly measured. |
| 87 | Sensor Reading | A measurement, determination, observation, assessment, or potentially other forms of output by a sensor component 102 in relation to a patient attribute 85. Examples of sensor readings 87 can include temperature, pH level, electrical conductivity, oxygen saturation and other data relating to one or more patient attributes 85. A sensor reading 87 can include within it data relating to the sensor component 102 that captured the sensor reading 87, such as a relative position 133 of the sensor component 102 with respect to other sensor components 102, the location 88 of the sensor component 102 with respect to the patient 90, the identity of the patient 90, and other potential patient attributes 85. |
| 88 | Location | A position on the patient 90 on which a sensor component 102 is placed and a sensor reading 87 is captured. In many embodiments of the apparatus 100, locations 88 are on the skin of the patient 90. |
| 89 | Cardiac Performance Indicator | An assessment generated by the apparatus 100 with respect to the cardiac performance of the patient 90. Examples of potential cardiac performance indicators 89 include an arterial perfusion indicator 91, a cardiac output estimate 95 and a systemic vascular resistance value 93. |
| 90 | Patient | A living organism, typically a human being. |
| 91 | Arterial Perfusion Indicator | An assessment generated by the apparatus 100 that relates to the delivery of blood to a capillary bed in biological tissue. Overperfusion is a condition where too much blood is delivered, and underperfusion is a condition where too little blood is delivered. An arterial perfusion indicator 91 is an example of a type of cardiac performance indicator 89. |
| 92 | Provider | A doctor, nurse, nurse practitioner, lab technician, physician assistant, paramedic, or other person involved in evaluating the health of the patient 90. |
| 93 | Systemic Vascular Resistance Value | A metric representing resistance and/or blockage to the flow of blood in a patient 90. System vascular resistance value 93 is an example of a potential cardiac performance indicator 89. |
| 95 | Cardiac Output Estimate | A metric representing the aggregate output of the heart and cardiovascular system of the patient 90. This is an example of a potential cardiac performance indicator 89. |
| 97 | Data Set | A collection of data. The processor component 110 can compare individual sensor readings 87 to derive a cardiac performance indicator 89. Entire sets 97 of sensor readings 87 can be used to derive a cardiac performance indicator 89. |
| 100 | Sensor Apparatus (or simply the Apparatus) | An assembly of components that includes two or more sensor components 102 and a processor component 110. The apparatus 100 provides for using two or more sensor components 102 to capture sensor readings 87 relating to patient attributes 85 and for using a processor component 110 to derive a cardiac performance indicator 89 from those sensor readings 87. |
| 102 | Sensor Component (or simply "Sensor") | A device that detects or measures a physical property. Sensor Components 102 can be defined with respect to the phenomenon that is measured/detected or by the mechanisms by which a sensor functions, i.e. electronic, mechanical, electro-mechanical, etc. Examples of different sensor components 102 that can be incorporated into the apparatus 100 include temperature sensors 140, pH sensors 139, electrical connectivity sensors 138 and oxygen saturation sensors 136. |
| 104 | Sensor Connector Component | A device or structure that secures two or more sensor components 102 together. An example of a sensor connector component 104 is a strip 142 used to secure the relative positions 133 of a single-file sequence of sensor components 102. |

TABLE 1-continued

| Element Number | Element Name | Description |
|---|---|---|
| 108 | Communication Component | A device that communicates the cardiac performance indicator 89, the sensor readings 87, and/or other information to a provider 92 or other user. In many embodiments, the processor component 110 is embedded into the communication component 108 |
| 110 | Processor Component | A component or subassembly within the apparatus 100 that includes a computer processor that performs the processing logic of one or more cardiac performance heuristics 116 to generate a cardiac performance indicator 89. |
| 112 | External IT System | An information technology system 112 used to treat the patient 90 that is outside the scope of the apparatus 100. The sensor readings 87 of the apparatus 100 can be integrated into broader and/or comprehensive systems being used to treat the patient 90. The Exterior System 112 can add to the factors that influence the creation of the cardiac performance indicator 89 derived for a particular patient 90. |
| 114 | User Controls | A physical or virtual mechanism by which a user of the apparatus 100 can impact the function of the apparatus 100. User controls 114 allow the apparatus 100 to receive inputs from users such as providers 92. |
| 115 | Display Format | An arrangement of information. The apparatus 100 can provide for providing users with access to data in a variety of different display formats 115. FIGS. 1f and 1g are examples of display formats 115 that may be useful. |
| 116 | Cardiac Performance Heuristic | A process by which a cardiac performance indicator 89 is derived from sensor readings 87 and potentially other types of inputs. |
| 120 | User Instruction | Operating configuration parameters submitted to the apparatus 100 through one or more user controls 114. A user instruction 120 is submitted to the apparatus 100 through a user control 114. |
| 122 | Alerts | A notification generated by the apparatus 100 in conjunction with a cardiac performance indicator 89. By way of example, a cardiac performance indicator 89 can selectively trigger an audio alarm, a text message, an e-mail, an automated phone call, or some other form of notification to a provider 92 or patient 90. |
| 124 | Controller Connector | A device that allows the apparatus 100 to interface with general purpose computers 126 such as smart phone 135, tablet computer 137, laptop computer, or other type of general purpose device. Examples of interface devices can be a component connector to a sensor strip 142 with a USB connector for connecting to the general purpose computer device |
| 126 | General Purpose Computer | A smart phone, tablet computer, laptop computer, desktop computer, or other form of computer device that provides users with the capability to add applications and to run software not limited to a specific purpose inherent to the device. |
| 130 | Moment in Time | A date/time identifier that can be associated with a sensor reading 87. By way of example, a gradient 132 of sensor readings 87 will often involve sensor measurements captured at the same time but from different locations 88 on the patient 90. |
| 131 | Frequency | A rate of occurrence that sensor readings 87 are captured by a sensor component 102. |
| 132 | Gradient | A vector of sensor readings 87 and the locations 88 (or in some instances relative positions 133) associated with those sensor readings 87. |
| 133 | Relative Position | A position of a sensor component 102 (and corresponding sensor readings 87) that is defined in respect to the other sensor components 102. For example, in a strip 142 of 10 sensor components 102, sensor #2 would be positioned between sensor #1 and sensor #3. The gradient 132 can be based on relative positions 133 as well as locations 88. |
| 134 | Threshold Value | A value that exists for the purposes of comparison with a cardiac performance indicator 89. An alert 122 can be automatically triggered by the processor component 110 when the cardiac performance indicator 89 has some mathematical relationship with respect to the threshold value 134, i.e. less than, less or equal to, greater than, greater than or equal to, etc. |
| 135 | Smart Phone | A general purpose computer 126 in the form of a cellular phone. |
| 136 | Oxygen Saturation Sensor | A sensor component 102 that measures or estimates the magnitude of oxygen saturation in the blood of a patient 90. |

TABLE 1-continued

| Element Number | Element Name | Description |
|---|---|---|
| 137 | Tablet | A general purpose computer 126 in the form of a portable tablet. |
| 138 | Electrical Conductivity Sensor | A sensor component 102 that detects and measures the magnitude of electrical conductivity on the skin of the patient 90. |
| 139 | pH Sensor | A sensor component 102 that measures the acidity of the skin of the patient 90. |
| 140 | Temperature Sensor | A sensor component 102 that measures temperature information. |
| 141 | Ambient Readings | A sensor measurement captured with respect to the exterior environment of the patient 90. |
| 142 | Sensor Strip | A physical strip that secures the position of two or more sensor components 102. |
| 144 | Wired Connection | A connection 149 involving a physical wire to exchange information between components. |
| 145 | Wireless Connection | A connection 149 that does not involve the use of a physical wire to exchange information between components. Virtually any form of wireless technology including but not limited to Bluetooth, WiFi, cell phone networks, etc. can be used to provide a wireless connection 145. |
| 146 | Controller | A device that provides for outputs from the apparatus 100 to the user. The controller 146 can also in some embodiments be used to convey instructions 120 to the apparatus 100. |
| 147 | Screen_(or Display Screen) | A visual display 147 similar to what is used on consumer electronics devices, such as a monitor, smart phone 135, or tablet 137. In some embodiments, the screen 147 is a touch screen that also functions as one or more user controls 114. |
| 148 | Button | An example of a type of user control 114. Buttons 148 can be virtual or physical. |
| 149 | Connection | A capability to communicate information between two different components, subassemblies, etc. |
| 160 | Foam Layer | A layer of insulation used with respect to a component of the apparatus 100. |
| 161 | Adhesive Layer | A layer of glue or other similar adhesive used to hold different components of the apparatus 100 together and/or secure the position of the apparatus 100 on the patient 90. |
| 162 | Peel Away Layer | A layer positioned on an adhesive layer 161 such that the removal of the peel away layer 162 exposes an adhesive layer 161 that can secure the position of the apparatus 100 on a location 88 of the patient 90. |
| 163 | Circuit Board | A board on which electronics can be mounted. In some embodiments, the sensor component 102 and/or processing component 110 are mounted on a circuit board 163. |
| 190 | Appendage | A limb of a patient 90, such as an arm or leg. |
| 191 | Core Location | A portion of an appendage 190 that is closest to the torso of the patient 90. |
| 192 | Extremity Location | A portion of an appendage 190 that is the farthest away from the torso of the patient, such as the fingers or toes. |

IX. Scope of the Disclosure

The description of the apparatus 100 and various components and subcomponents provided above should be understood to include all novel and non-obvious combination of elements described herein, and claims may be presented in this or a later application to any novel non-obvious combination of these elements. Moreover, the foregoing embodiment is illustrative, and no single feature or element is essential to all possible combinations that may be claimed in this or a later application.

The invention claimed is:

1. An apparatus for detecting a cardiac performance indicator, comprising:
a first plurality of temperature sensors arranged on a first strip;
a second plurality of temperature sensors arranged on a second strip; and
a controller configured to receive data from the first and second plurality of temperature sensors, analyze the data to determine a temperature gradient along the first and second strips, compare the temperature gradient along the first strip and the temperature gradient along the second strip, and determine the cardiac performance indicator based on the comparison, wherein the cardiac performance indicator is one of a cardiac output estimate, an arterial profusion indicator, and a systemic vascular resistance value.

2. The apparatus of claim 1, further comprising an adhesive layer configured to facilitate positioning the first and second strips on the skin of a patient.

3. The apparatus of claim 1, wherein the controller is configured to perform a cardiac performance heuristic based on the cardiac performance indicator.

4. The apparatus of claim 3, wherein the cardiac performance heuristic includes communicating an alert.

5. The apparatus of claim 1, wherein the controller is situated on one of the first and second strips, and further comprising a wired connection between the controller and the plurality of sensors.

6. The apparatus of claim 1, wherein the controller is configured to receive a user input relating to a frequency at which the plurality of temperature sensors capture data and control the plurality of temperature sensors based on the user input.

7. The apparatus of claim 1, further comprising a display screen configured to display the temperature gradient along on of the first and second strips.

8. The apparatus of claim 1, wherein at least one of the plurality of temperature sensors is configured to sense an ambient temperature.

9. A method for detecting a cardiac performance indicator of a patient, comprising:
- positioning a first sensor strip that includes a first plurality of skin temperature sensors on an appendage of a patient;
- capturing a first set of skin temperature readings from the first plurality of skin temperature sensors;
- determining a temperature gradient along the strip based on the first set of skin temperature readings;
- positioning a second sensor strip that includes a second plurality of skin temperature sensors on an appendage of a patient;
- capturing a second set of skin temperature readings from the second plurality of skin temperature sensors;
- determining a temperature gradient along the second strip based on the second set of skin temperature readings from the second plurality of skin temperature sensors; and
- determining a cardiac output estimate based on a comparison of the temperature gradient along the first and second strips.

10. The method of claim 9, further comprising comparing a systemic vascular resistance value to a predetermined threshold systemic vascular resistance value.

11. The method of claim 9, further comprising displaying the temperature gradient along one of the first and second strips.

12. The method of claim 9, further comprising performing a cardiac performance heuristic based on the cardiac output estimate.

13. The method of claim 12, wherein the cardiac performance heuristic includes communicating an alert.

14. The method of claim 13, wherein the alert is communicating to a healthcare provider of the patient.

15. The method of claim 9, further comprising comparing one or more temperatures of one of the first and second sets of skin temperature readings to a predetermined threshold temperature.

* * * * *